United States Patent
Salbeck et al.

(10) Patent No.: US 6,822,094 B2
(45) Date of Patent: Nov. 23, 2004

(54) SPIRO COMPOUNDS AND THEIR USE

(75) Inventors: Josef Salbeck, Kelkheim (DE); Donald Lupo, Frankfurt (DE)

(73) Assignee: Aventis Research & Technologies, GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 10/205,945

(22) Filed: Jul. 26, 2002

(65) Prior Publication Data
US 2003/0111107 A1 Jun. 19, 2003

Related U.S. Application Data

(63) Continuation of application No. 09/381,318, filed as application No. PCT/EP98/01559 on Mar. 18, 1998, now abandoned.

(30) Foreign Application Priority Data

Mar. 20, 1997 (DE) .......................... 197 11 714

(51) Int. Cl.$^7$ .................... C07D 241/36; C07D 209/54; C07D 221/00; C07C 13/465

(52) U.S. Cl. .................... 544/230; 546/15; 548/136; 548/143; 548/147; 548/216; 548/262.2; 548/407; 548/411; 564/426; 585/27; 514/409; 514/410; 514/411; 514/183

(58) Field of Search ................ 514/183, 409, 514/410, 411; 544/230; 546/15; 548/407, 411, 300.7; 564/426

(56) References Cited

U.S. PATENT DOCUMENTS

| | | | |
|---|---|---|---|
| 5,084,365 A | 1/1992 | Gratzel et al. ............... 429/11 |
| 5,683,833 A | 11/1997 | Haussling et al. .......... 429/192 |
| 5,840,217 A | 11/1998 | Lupo et al. ................. 252/583 |
| 5,885,368 A | 3/1999 | Lupo et al. ................. 136/263 |

FOREIGN PATENT DOCUMENTS

| | | | |
|---|---|---|---|
| EP | 333641 | * | 9/1989 |
| EP | 0 333 641 A1 | | 9/1989 |
| EP | 0 676 461 A2 | | 10/1995 |
| EP | 676461 | * | 10/1995 |
| EP | 0 718 858 A2 | | 6/1996 |
| WO | WO 97/10617 | | 3/1997 |

\* cited by examiner

Primary Examiner—Richard L. Raymond
Assistant Examiner—Sudhaker B. Patel
(74) Attorney, Agent, or Firm—Frommer Lawrence & Haug LLP

(57) ABSTRACT

Spiro compounds of the formula (I),

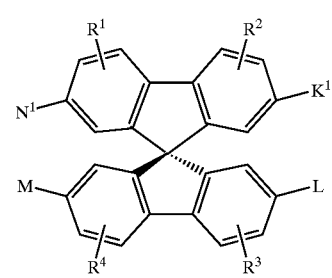

in which at least one of the radicals $K^1$, L, M, $N^1$, $R^1$, $R^2$, $R^3$, $R^4$ is one of the following groups

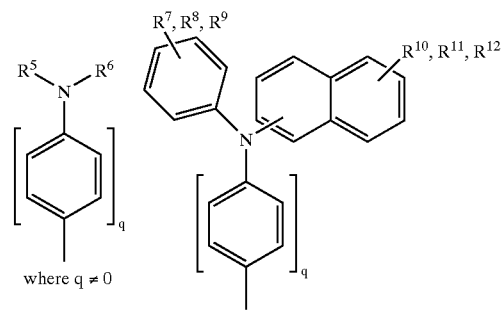

where q ≠ 0

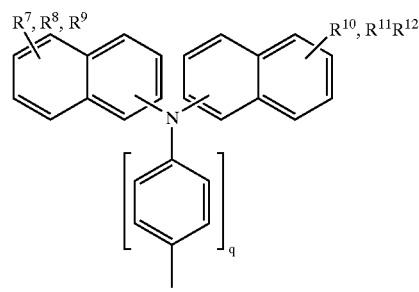

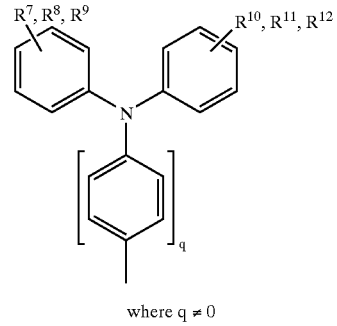

where q ≠ 0

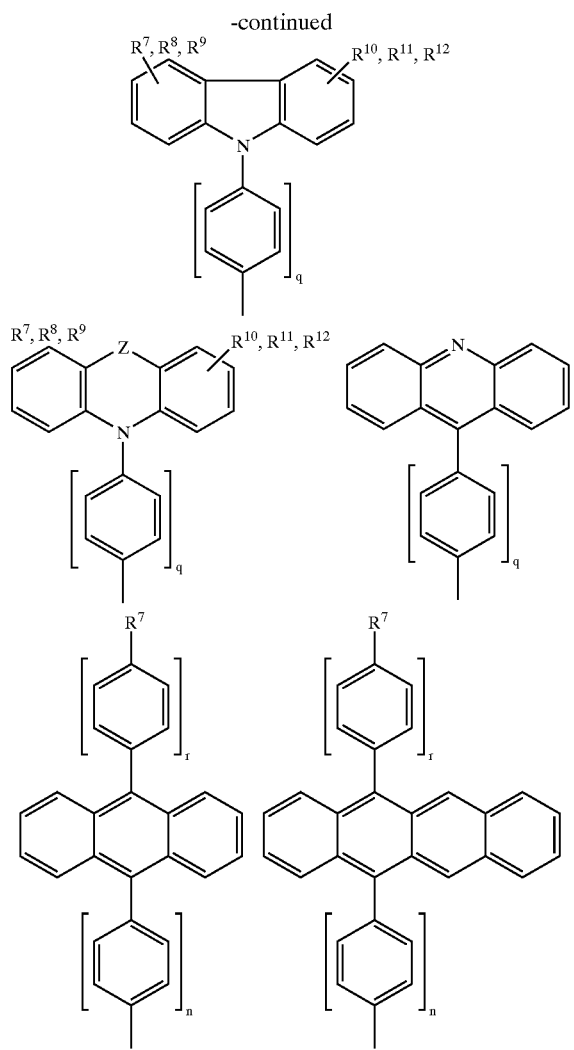
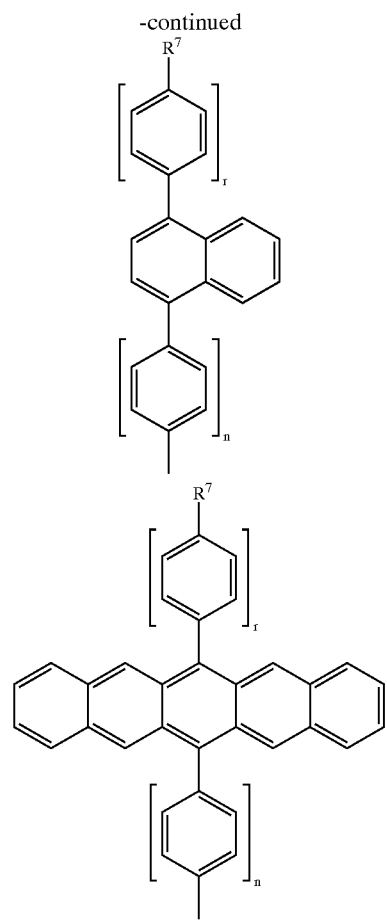
are suitable as charge transport materials, in particular for photovoltaic cells, and as electroluminescence materials.
5 Claims, No Drawings

SPIRO COMPOUNDS AND THEIR USE

RELATED APPLICATIONS

This application is a continuation of application U.S. Ser. No. 09/381,318, filed Dec. 1, 1999, now abandoned, which in turn is a 371 of PCT/EP98/01559, filed Mar. 18, 1998, which in turn claims priority to German application Serial No. 197 11 714.7, filed Mar. 20, 1997.

Owing to the increasing global demand for electric energy and the limited reserves of coal, oil and gas, which in addition liberate the greenhouse gas $CO_2$ when they are burnt, the generation of electric power from sunlight has attracted increased interest in recent years.

EP-A 0 333 641 describes a photoelectrochemical cell which comprises a nanoporous metal oxide semiconductor, i.e. a semiconductor which has an extremely roughened surface and thus an increased surface area. The charge transport between semiconductor/chromophore layer and counterelectrode in this cell occurs via an electrolyte solution. Although good results are achieved using such cells, the property profile of such a device is still capable of significant improvement.

EP-A 0 718 858 discloses such a cell having a liquid crystal charge transport material in place of an electrolyte. However, the apparent quantum yields achieved are still in need of improvement.

It has now surprisingly been found that certain derivatives of spirobifluorene are very suitable as charge transport material for photovoltaic cells.

Some structurally different spirobifluorene derivatives are described, for example, in U.S. Pat. No. 5,026,894, J. M. Tour et al. J. Am. Chem. Soc. 112 (1990) 5662 and J. M. Tour et al. Polym. Prepr. (1990) 408 as coupling elements for polymeric, organic semiconductors and are proposed as materials for molecular electronics.

EP-A 0 676 461 describes the use of spiro compounds of the following formula,

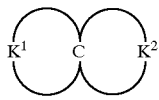

where $K^1$ and $K^2$ are, independently of one another, conjugated systems, in electroluminescence devices.

Use in photovoltaic cells cannot be deduced therefrom.

The invention accordingly provides spiro compounds of the formula (I)

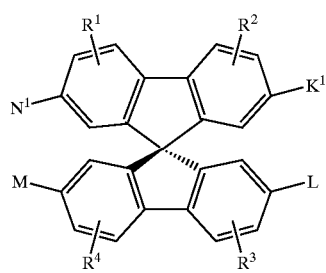

where the symbols have the following meanings:

$K^1$, L, M, $N^1$, $R^1$, $R^2$, $R^3$, $R^4$ are identical or different and are each a) hydrogen, $-NO_2$, $-CN$, $-F$ or $-Cl$, b) a straight-chain or branched alkyl radical having from 1 to 20 carbon atoms, where b1) one or more nonadjacent $CH_2$ groups can be replaced by $-O-$, $-S-$, $-CO-O-$, $-O-CO-$, $-O-CO-O-$, $NR^5$ or $-Si(CH_3)_2-$ and/or b2) one or more $CH_2$ groups can be replaced by $-CH=CH-$, $-C\equiv C-$, 1,4-phenylene, 1,4-cyclohexylene or 1,3-cyclopentylene and/or b3) one or more H atoms can be replaced by F and/or Cl, and/or c) one of the following groups:

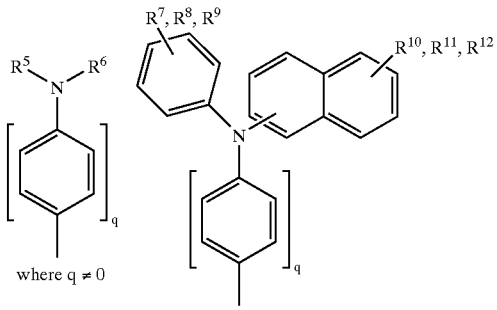

where q ≠ 0

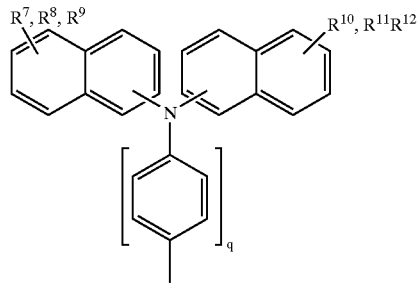

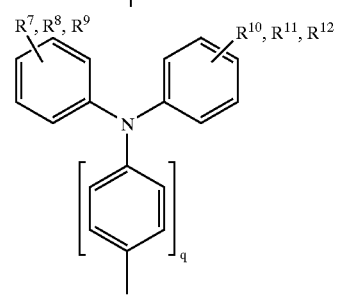

where q ≠ 0

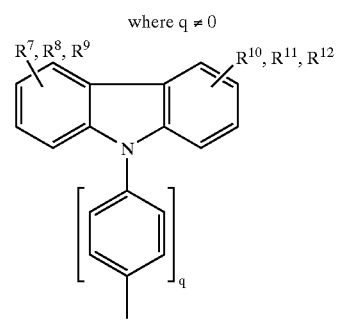

-continued

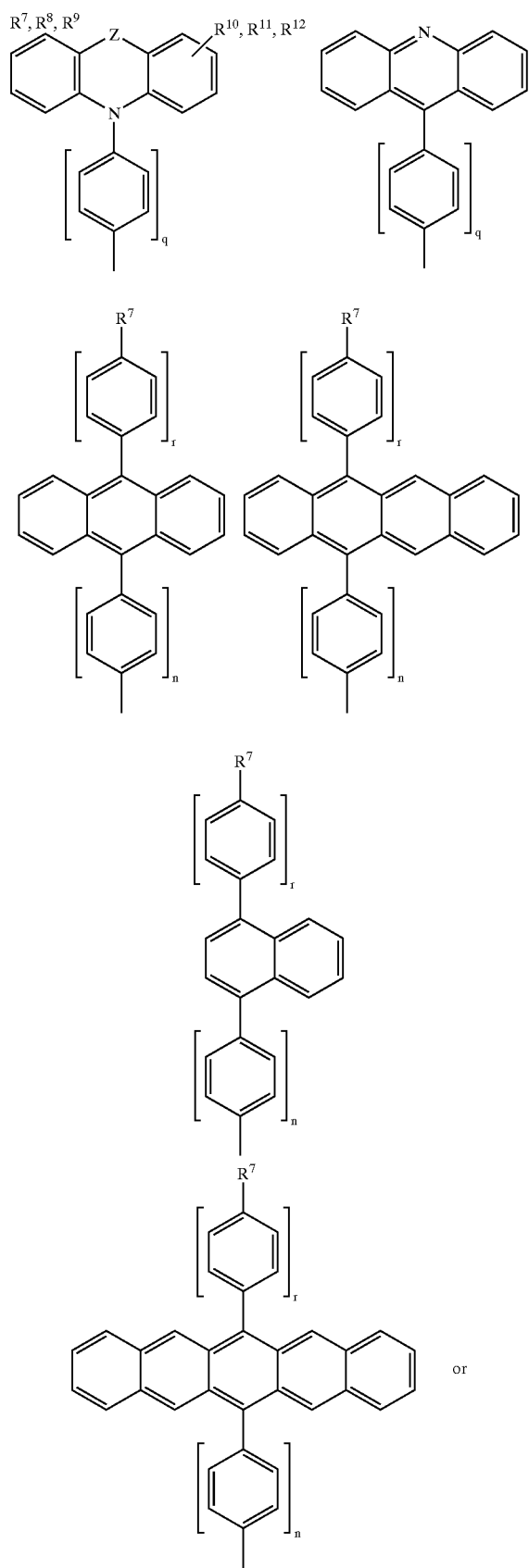

d) one of the following groups:

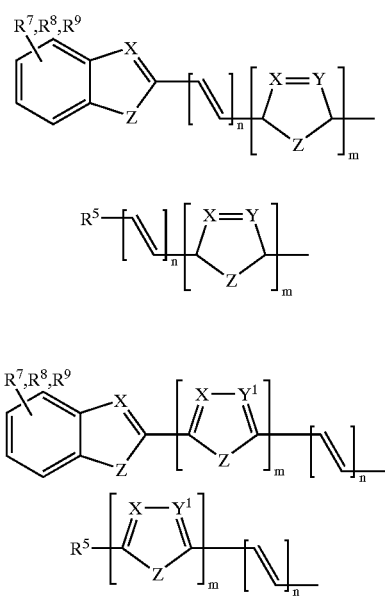

with the proviso that at least one, preferably at least two, of the radicals $K^1$, L, M, $N^1$, $R^1$, $R^2$, $R^3$, $R^4R$ is one of the groups listed under c);

X, $Y^1$ are in each case identical or different and are $=CR^7—$ or $=N—$;

Z is $—O—$, $—S—$, $—NR^5—$, $—CRR—$, $—CR=CR—$ or $—CR=N—$;

$R^5$, $R^6$ are in each case identical or different and are each
  a) hydrogen,
  b) a straight-chain or branched alkyl radical having from 1 to 20 carbon atoms, where
    b1) one or more nonadjacent $CH_2$ groups which are not bound to nitrogen can be replaced by $—O—$, $—S—$, $—CO—O—$, $—O—CO—$, $—O—CO—O—$ or $—Si(CH_3)_2—$ and/or
    b2) one or more $CH_2$ groups can be replaced by $—CH=CH—$, $—C\equiv C—$, cyclopropane-1,2-diyl, 1,4-phenylene, 1,4-cyclohexylene or 1,3-cyclopentylene and/or
    b3) one or more H atoms can be replaced by F and/or Cl and/or
    b4) $R^5$ and $R^6$ together can also form a ring;
  c) phenyl, biphenyl, 1-naphthyl, 2-naphthyl, 2-thienyl, 2-furanyl;

$R^7$, $R^8$, $R^9$, $R^{10}$, $R^{11}$, $R^{12}$ are identical or different and are each
  a) hydrogen, $—CN$, $—F$, $NO_2$ or $—Cl$,
  b) a straight-chain or branched alkyl radical having from 1 to 20 carbon atoms, where
    b1) one or more nonadjacent $CH_2$ groups can be replaced by $—O—$, $—S—$, $—CO—O—$, $—O—CO—$, $—O—CO—O—$, $NR^5$ or $—Si(CH_3)_2—$ and/or
    b2) one or more $CH_2$ groups can be replaced by $—CH=CH—$, $—C\equiv C—$, cyclopropane-1,2-diyl, 1,4-phenylene, 1,4-cyclohexylene or 1,3-cyclopentylene and/or
    b3) one or more H atoms can be replaced by F and/or Cl;
  c) phenyl, biphenyl, 1-naphthyl, 2-naphthyl, 2-thienyl, 2-furanyl, $—O$-phenyl, $—O$-biphenyl, $—O$-1-naphthyl, $—O$-2-naphthyl, $—O$-2-thienyl, $—O$-2-furanyl, m, n, p, q, r are in each case identical or different and are 0, 1, 2, 3, 4, 5 or 6 preferably 0, 1, 2, 3, 4, particularly preferably 0, 1, 2, or 3.

The compounds of the formula (II) are preferably amorphous and have high glass transition temperatures.

Preference is given to spirobifluorene derivatives of the formulae (II) a–c

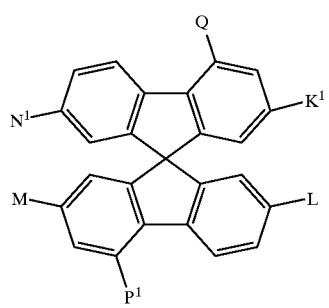
(II)

where the symbols have the following meanings:
II.a) $K^1$=L=M=$N^1$ and is selected from the group consisting of:

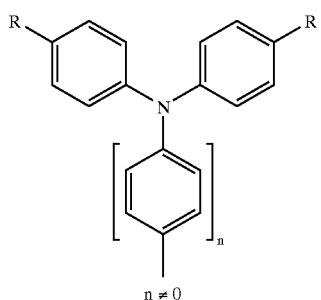

n ≠ 0

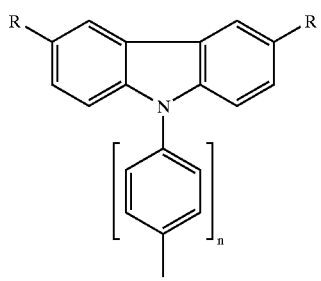

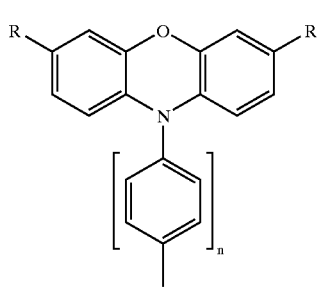

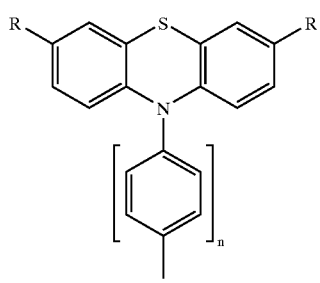

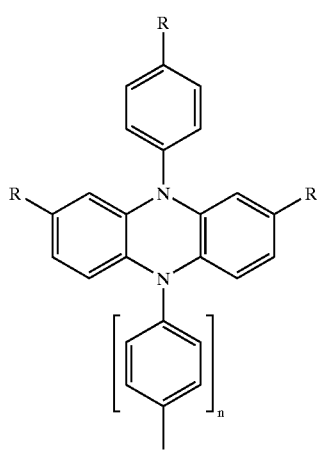

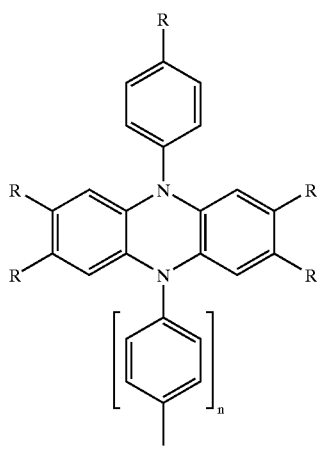

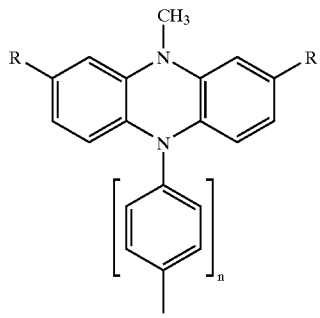

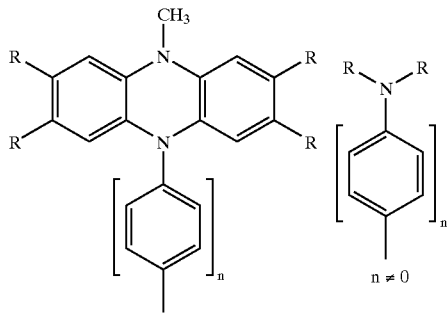
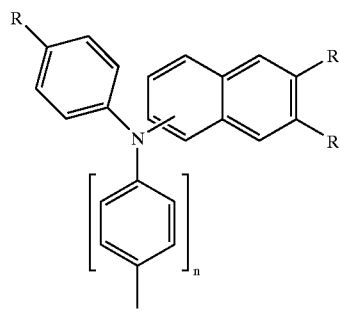
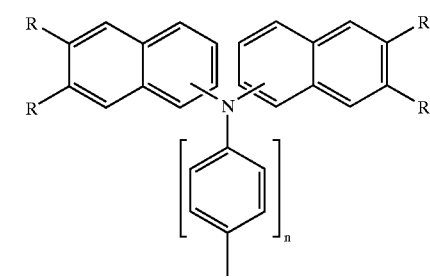
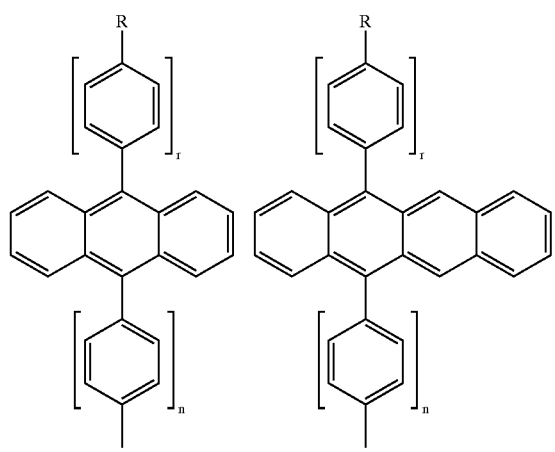
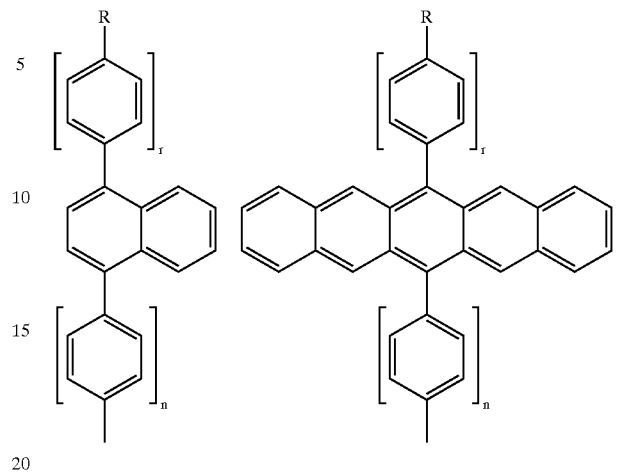

R are identical or different and are H, alkyl, —O-alkyl, —S-alkyl, each having from 1 to 20 carbon atoms, preferably from 1 to 4 carbon atoms, phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl, —O-2-furanyl, CN, $NR_2$, where —O-alkyl/aryl, —S-alkyl/aryl, CN, $NO_2$ must not be bound to nitrogen; n=0, 1, 2, 3, 4, and Q, $P^1$ are identical or different and are selected from the group consisting of:

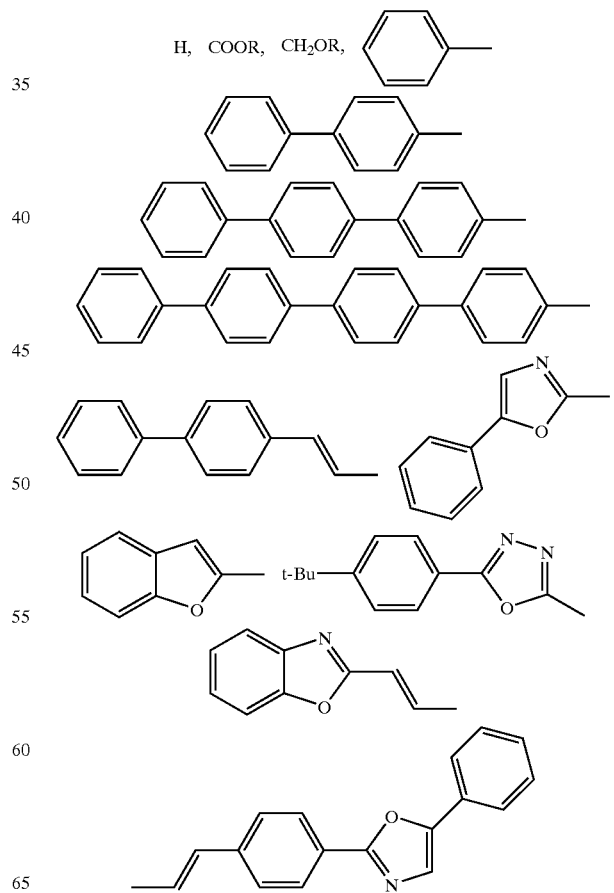

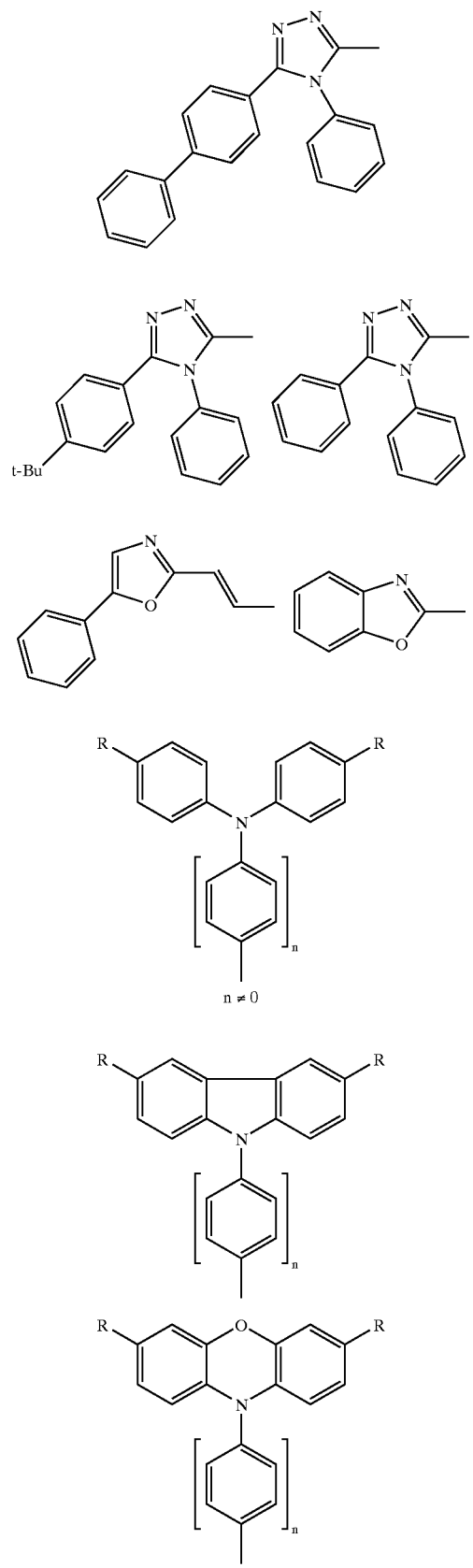
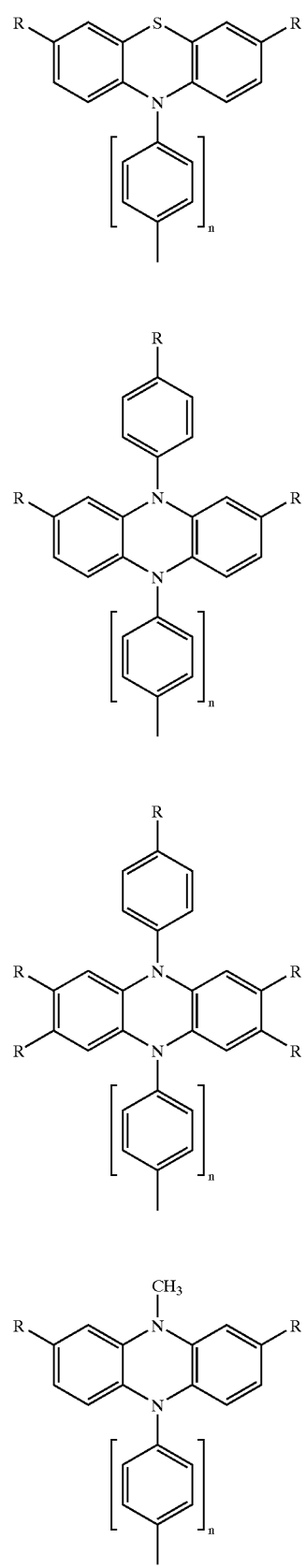

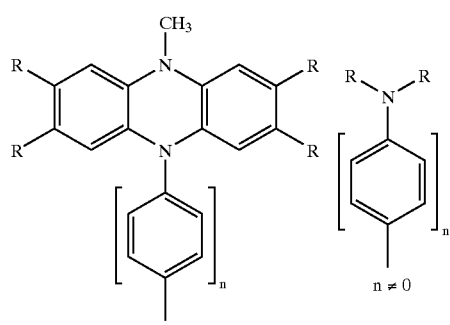
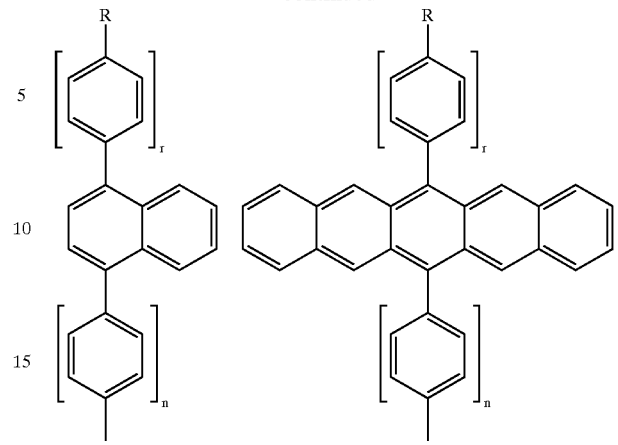
where the symbols and indices are as defined above,
II.b) $K^1 = N^1$ and is selected from the group consisting of:
II.b) $K^1 = N^1$ and is selected from the group consisting of:
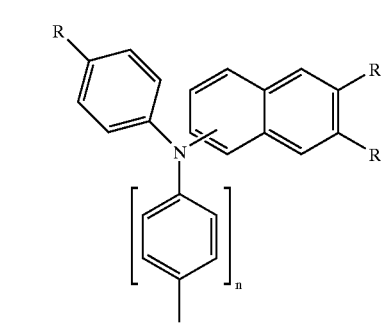
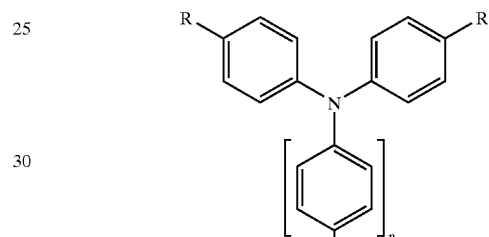
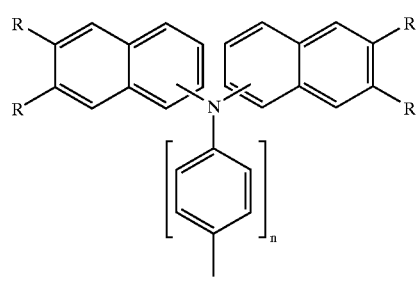
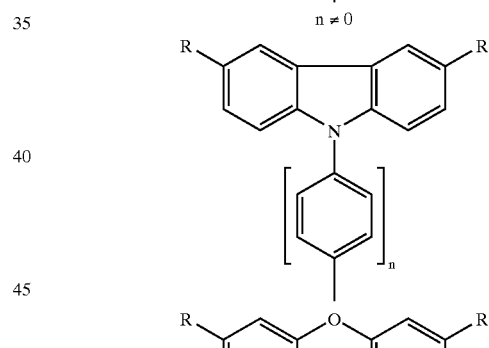
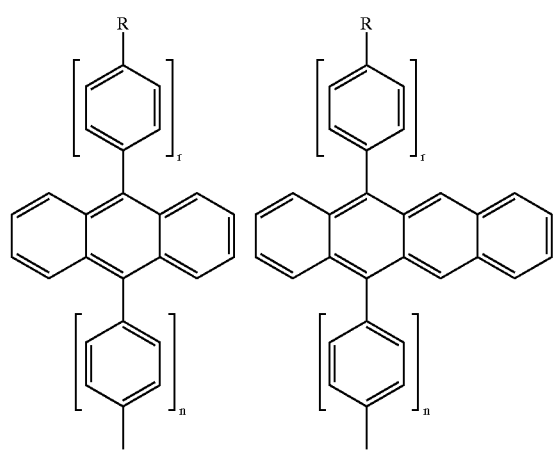
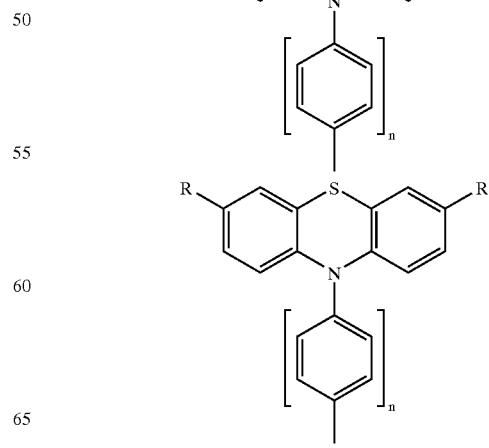

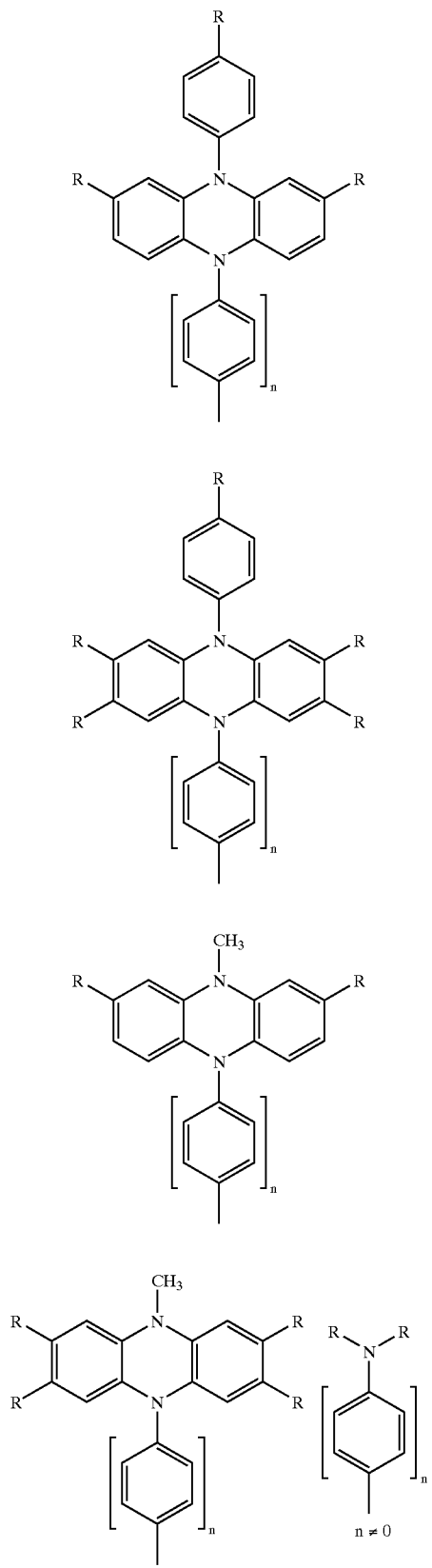
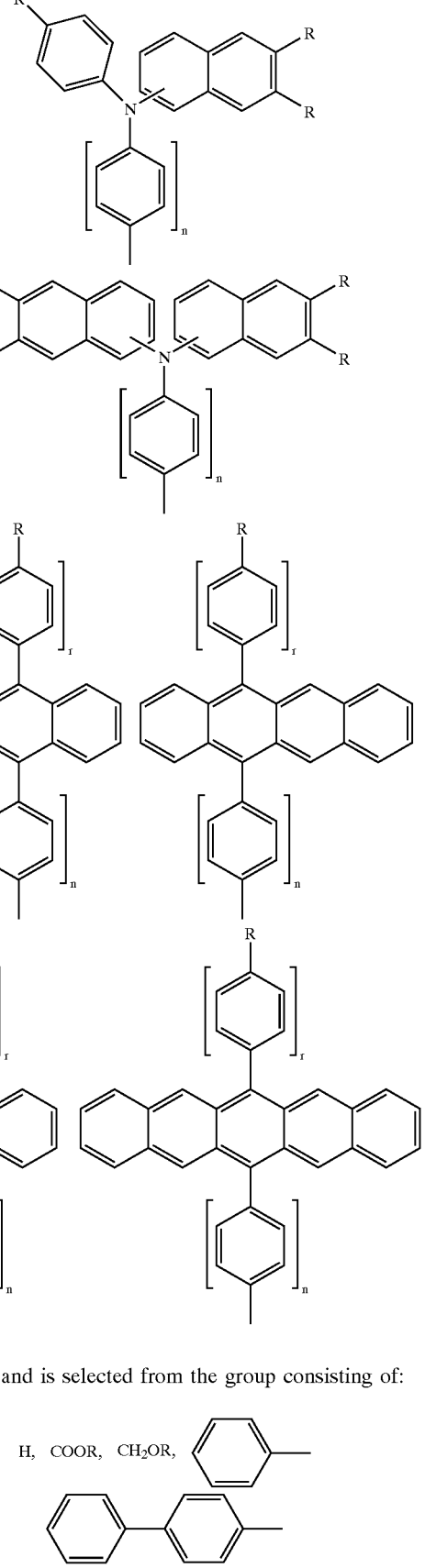
and L═M and is selected from the group consisting of:
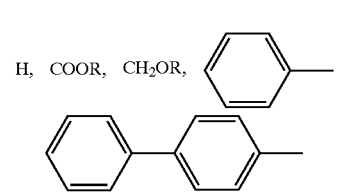

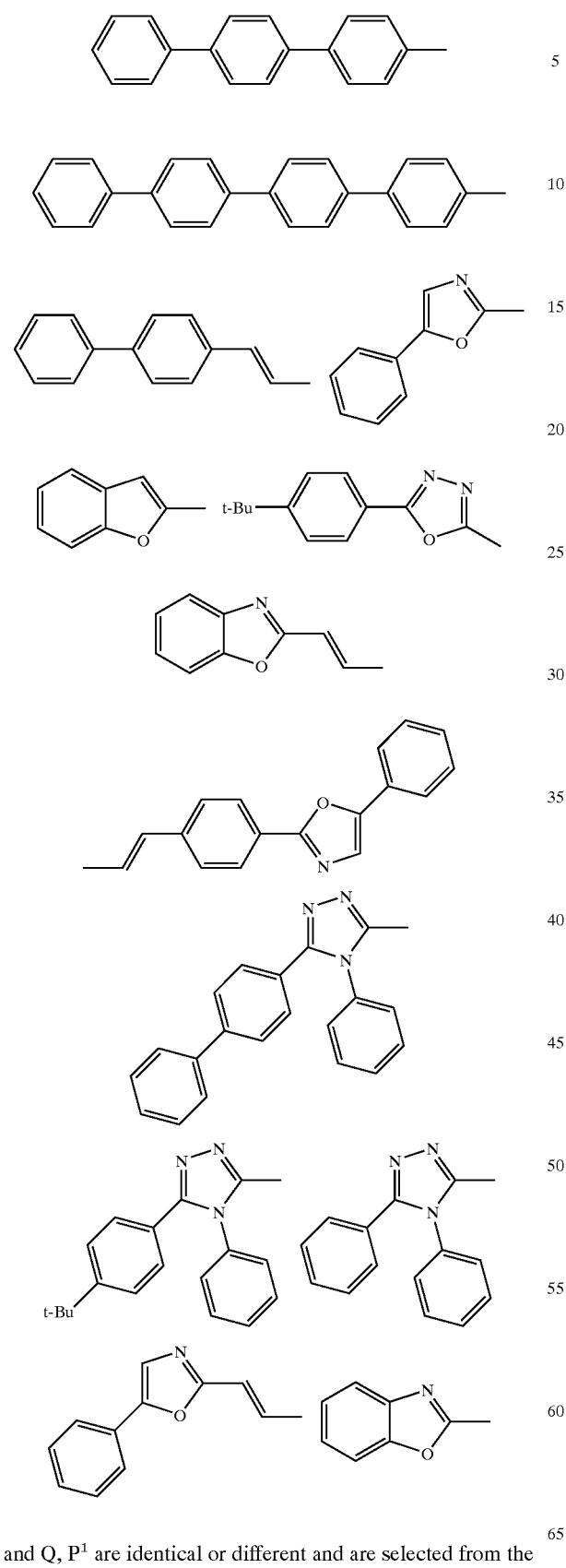
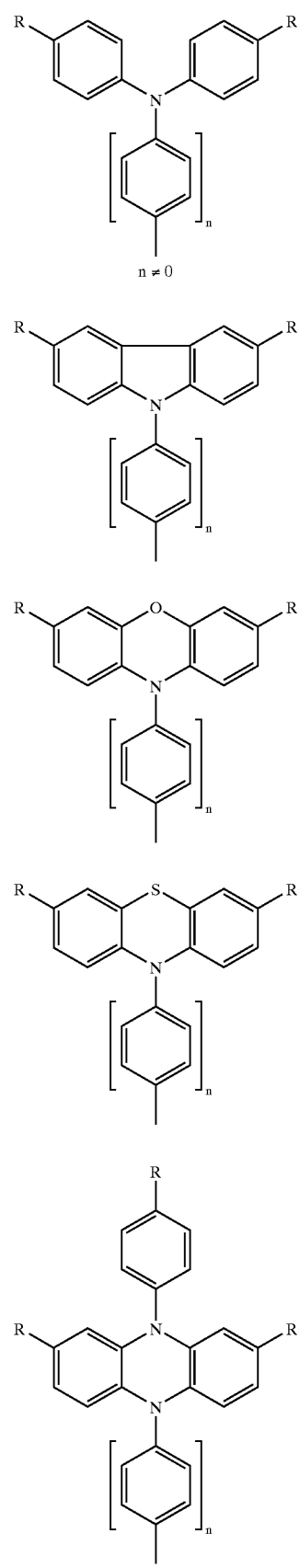
and Q, P¹ are identical or different and are selected from the group consisting of:

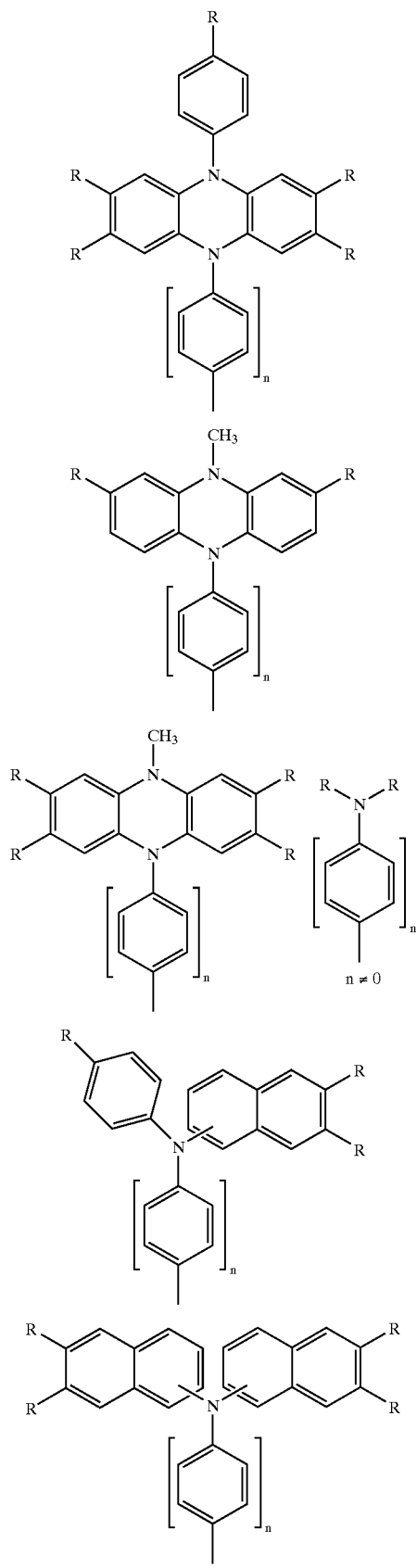
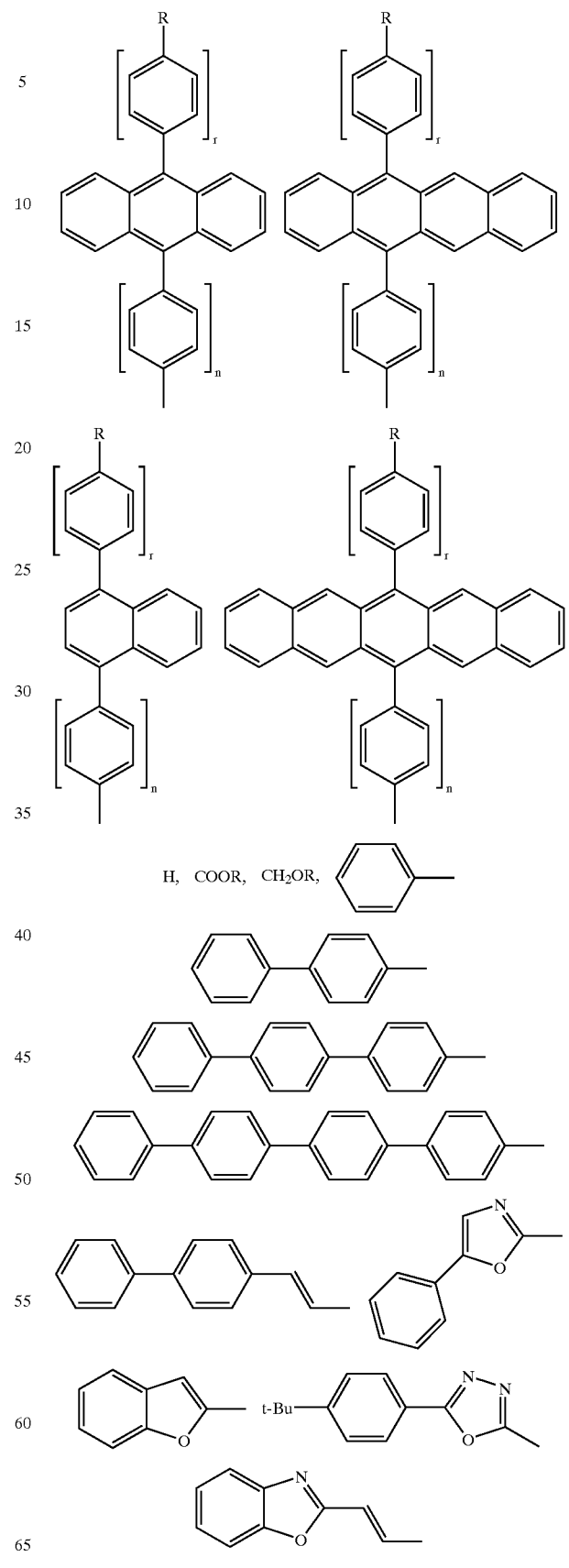

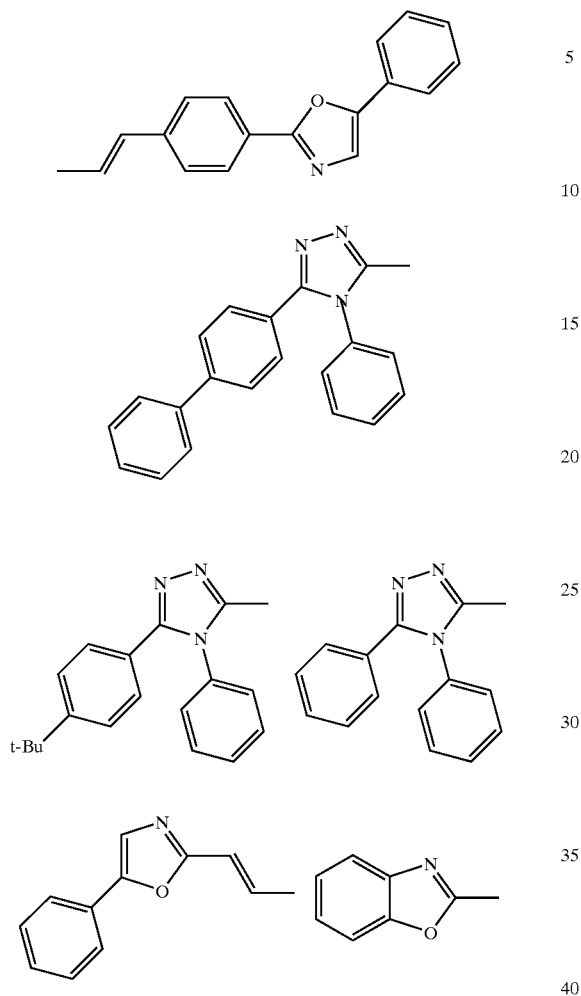
where the symbols and indices are as defined above;
IIc) $K^1$=M and is selected from the group consisting of:
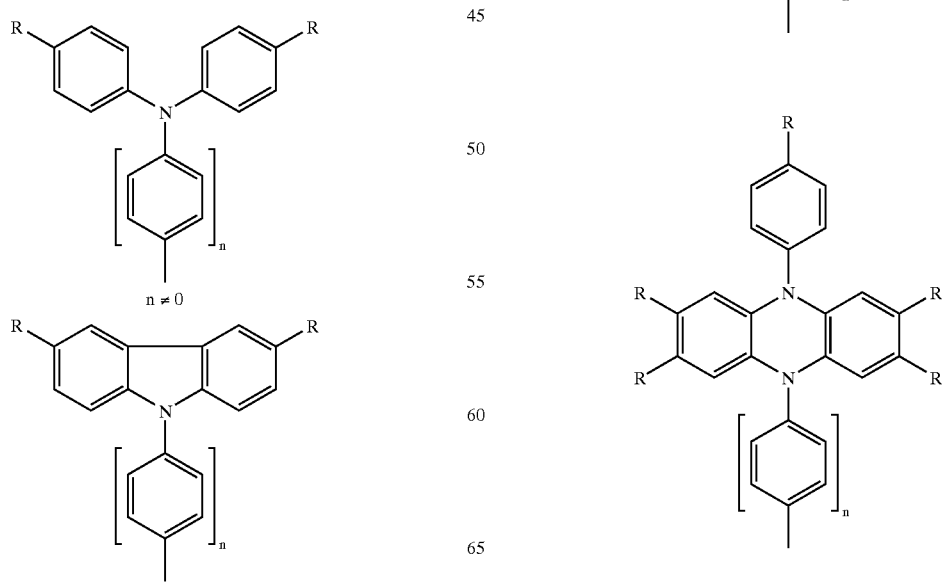

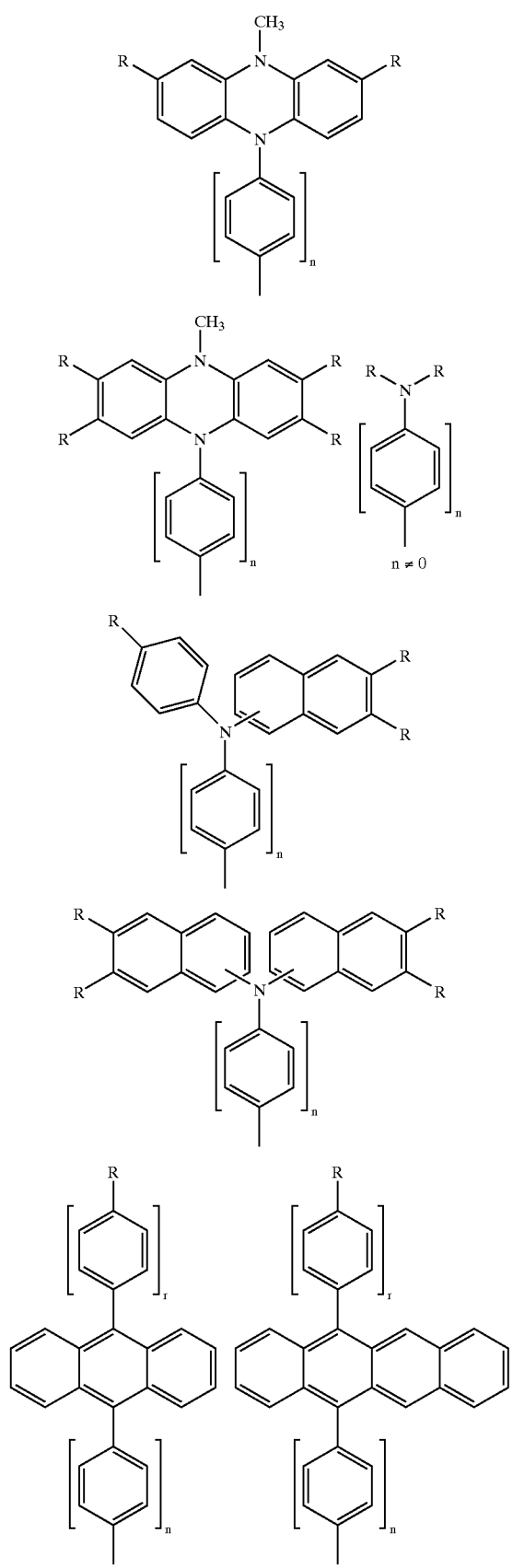
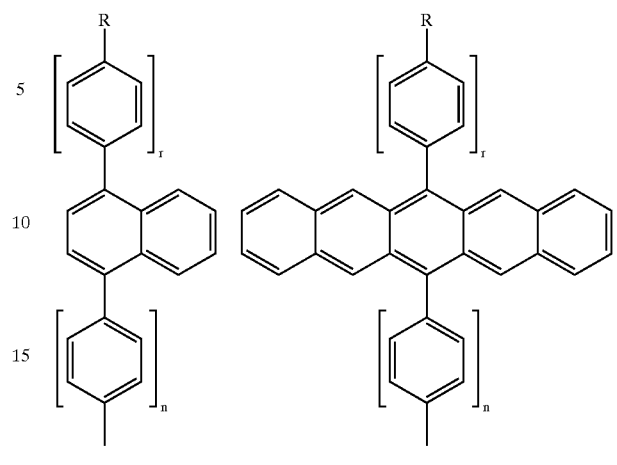
and M=N[1] and is selected from the group consisting of:
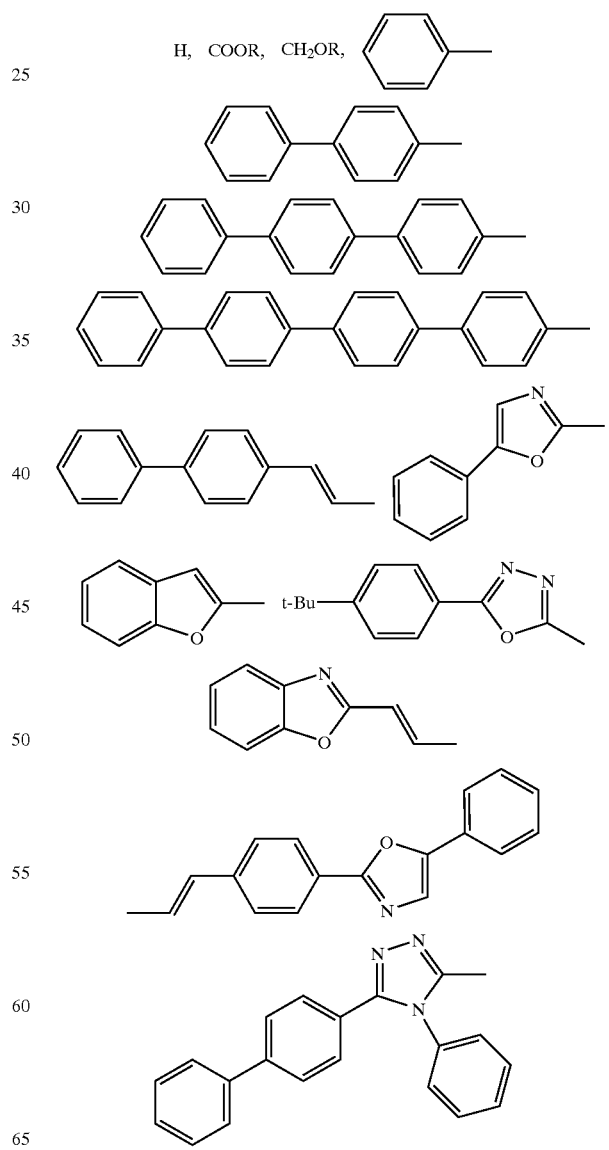

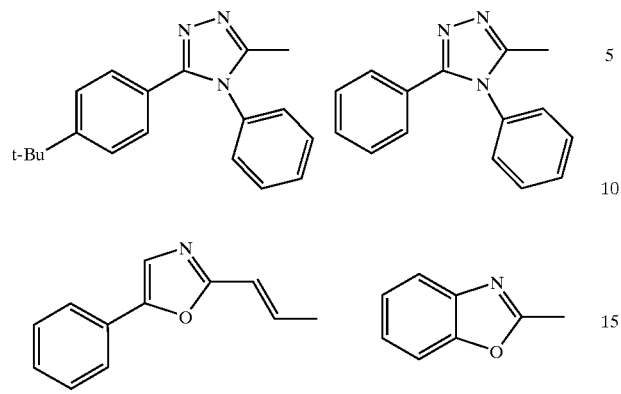
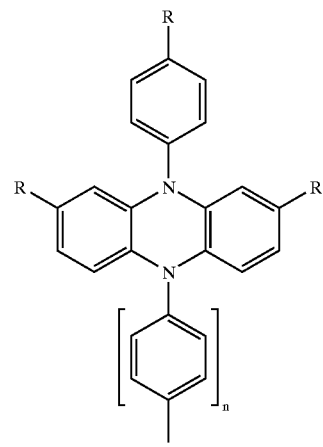
and Q, P¹ are identical or different and are selected from the group consisting of:
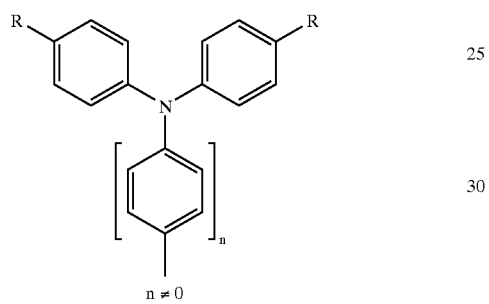
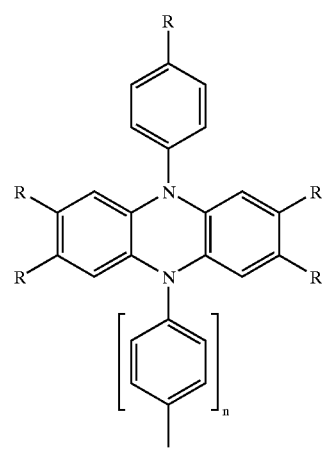
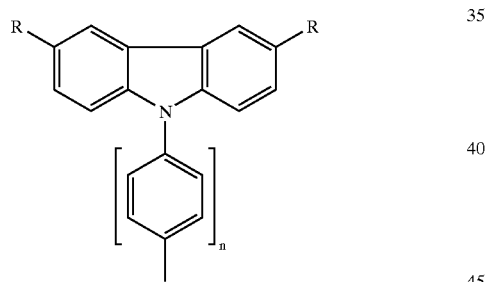
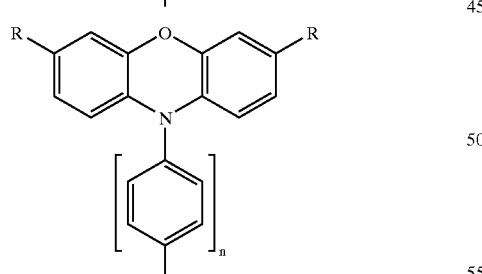
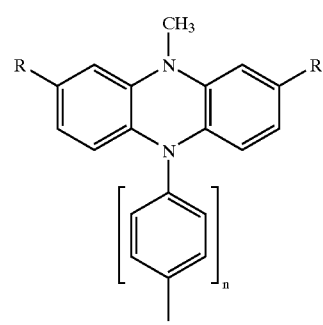
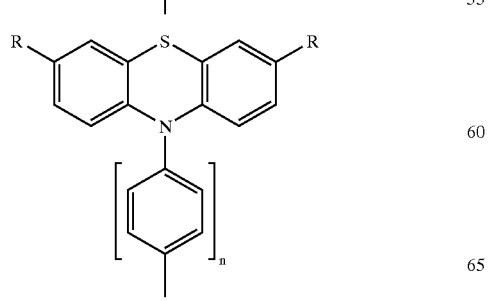
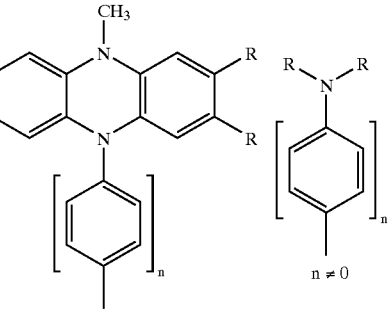

-continued
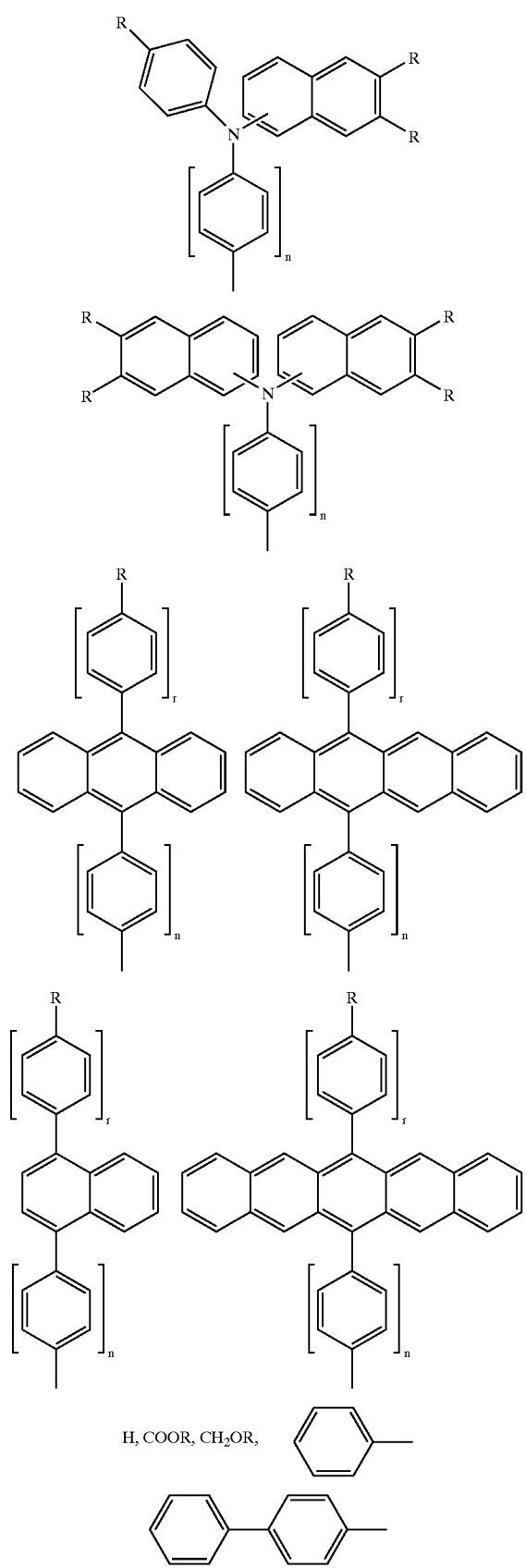
H, COOR, CH₂OR,
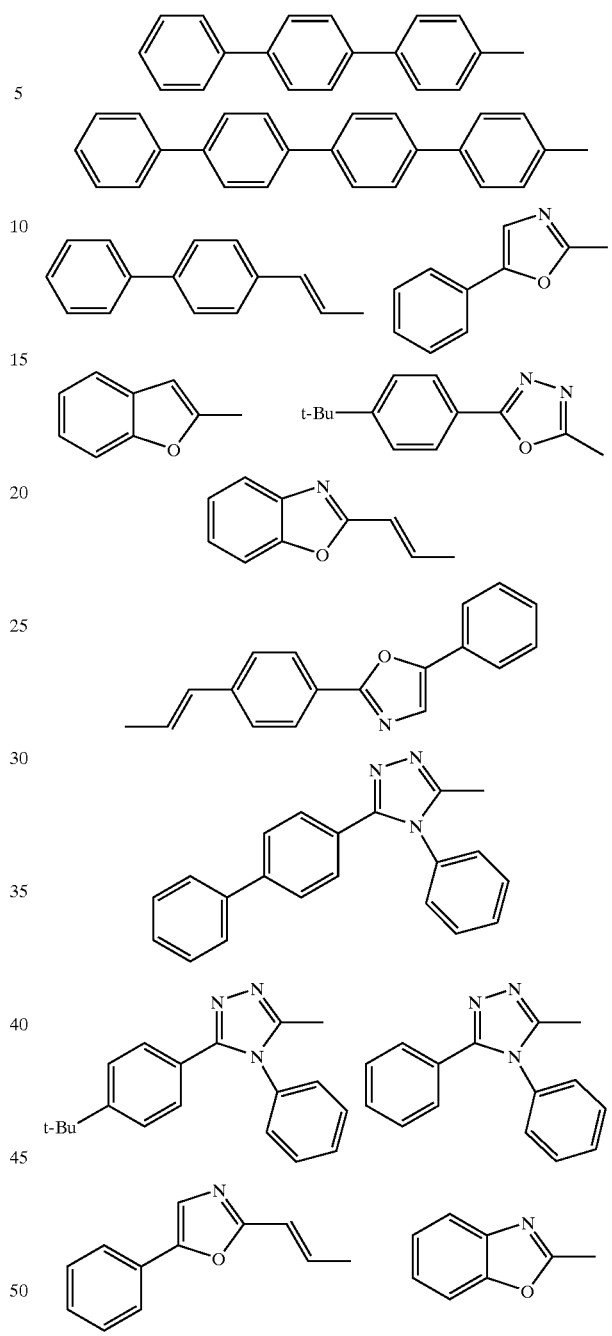
where the symbols and indices are as defined above.
Particular preference is given to the following compounds of the formula (II):
IIaa) $K^1=L=M=N^1$ and is selected from the group consisting of:

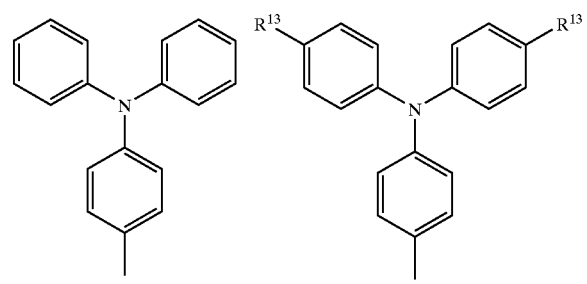
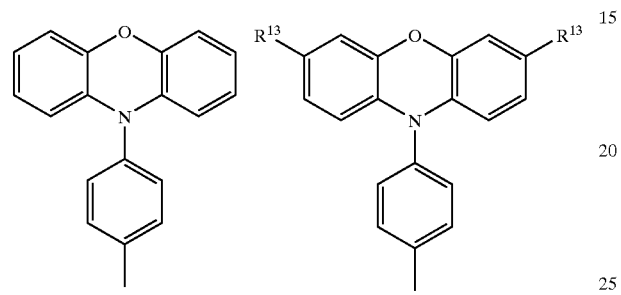
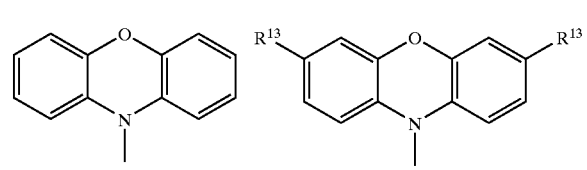
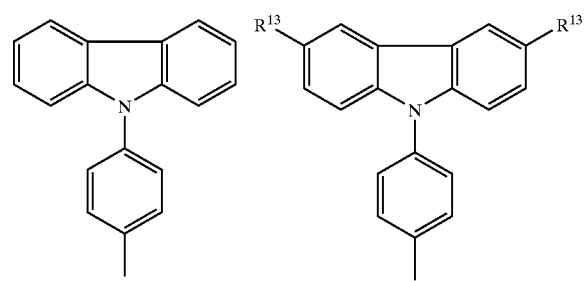
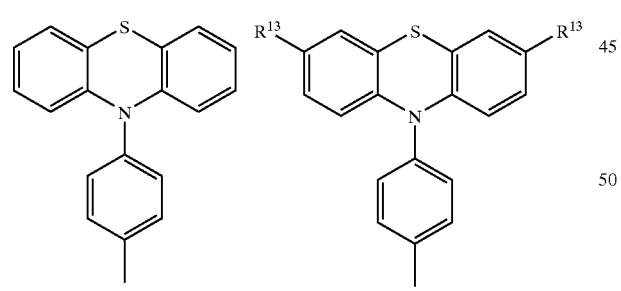
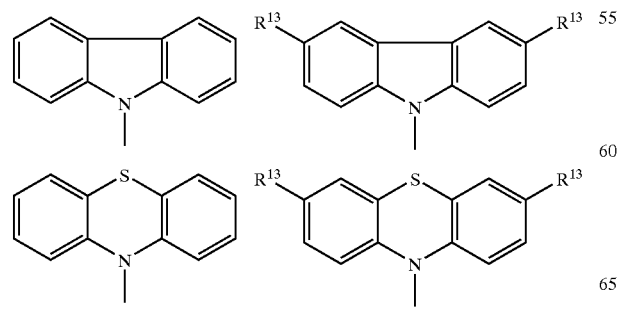
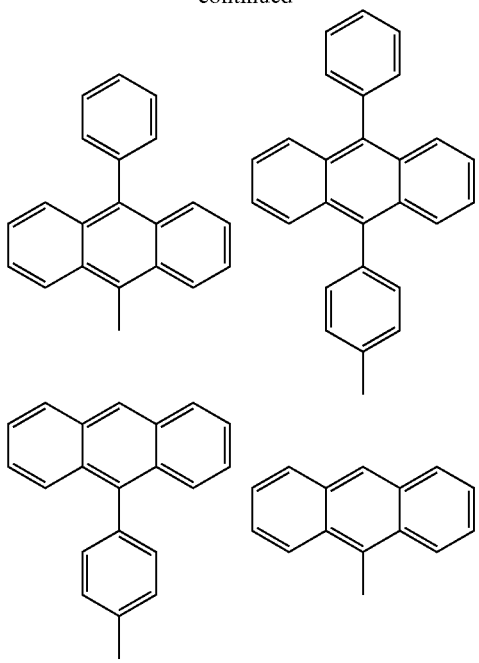
where R$^{13}$ is —O—CH$_3$, —O—C$_2$H$_5$, —S—CH$_3$, —S—C$_2$H$_5$, preferably —O—CH$_3$, —S—CH$_3$, particularly preferably —O—CH$_3$;
and Q=P$^1$ and is selected from the group consisting of:
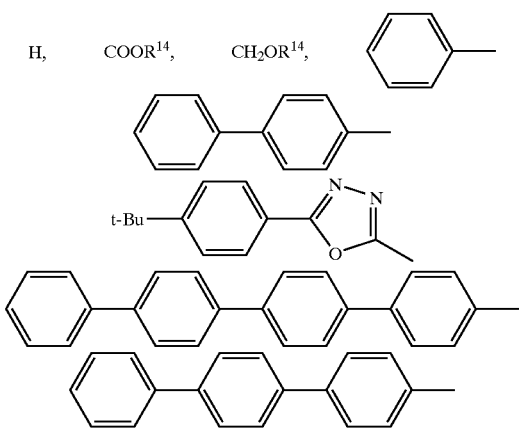
where R$^{14}$ is a straight-chain or branched alkyl group having from 1 to 12, preferably from 1 to 4, carbon atoms;
II.ba) K$^1$=M=N$^1$=Q=P$^1$ and is selected from the group consisting of:
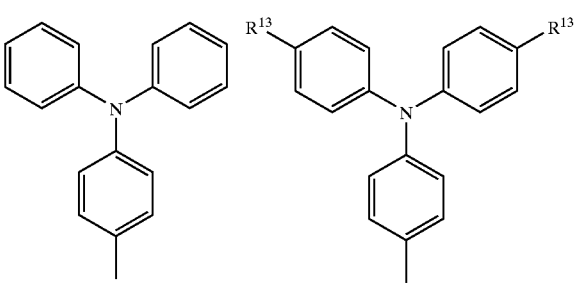

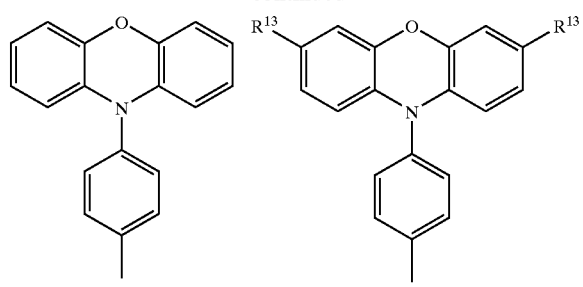
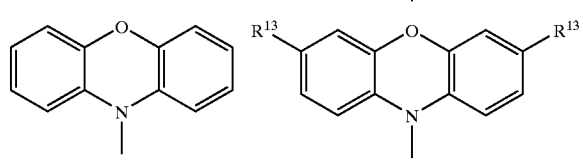
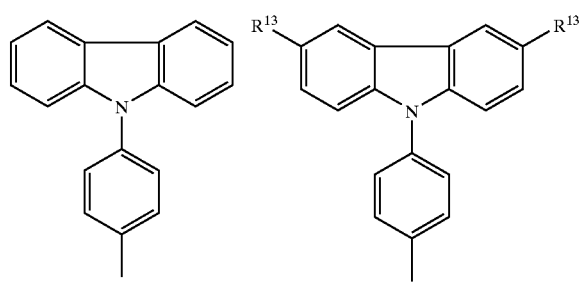
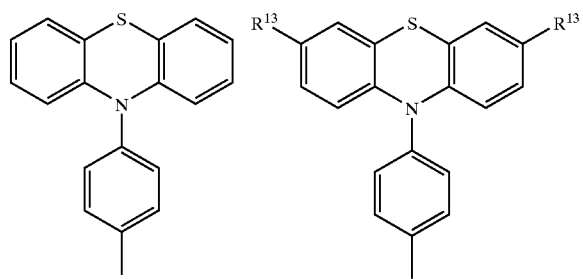
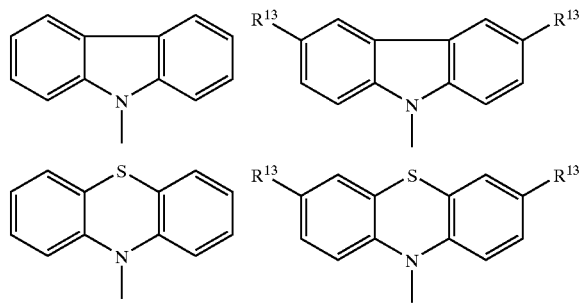
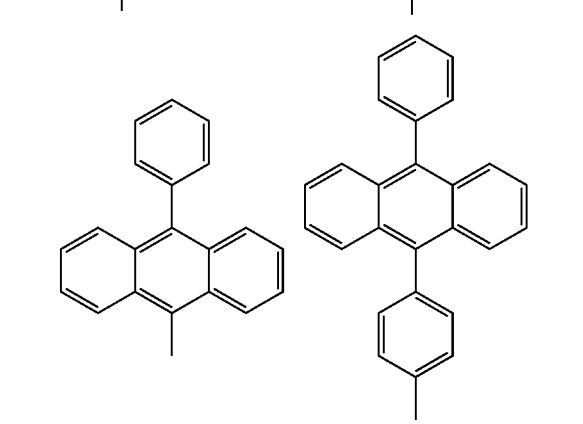
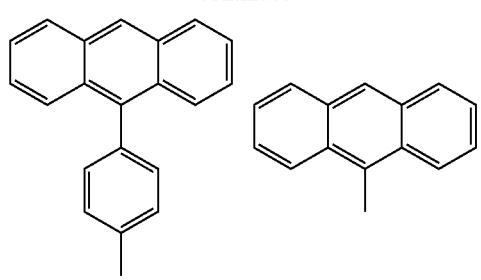
where $R^{13}$ is as defined above;
II.ca) $K^1=L=M=N^1$ and is selected from the group consisting of:
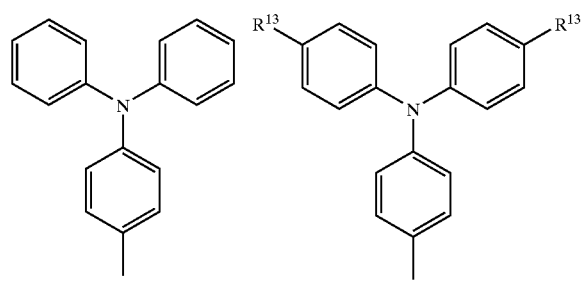
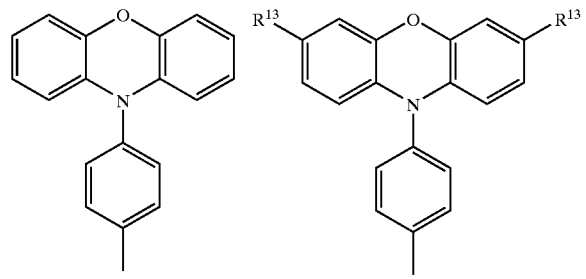
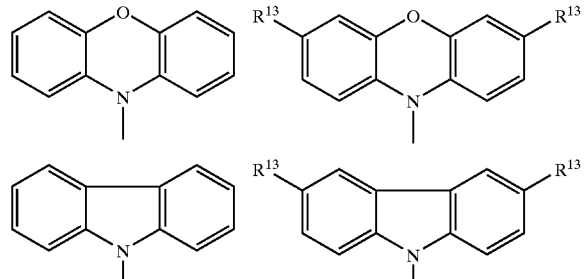
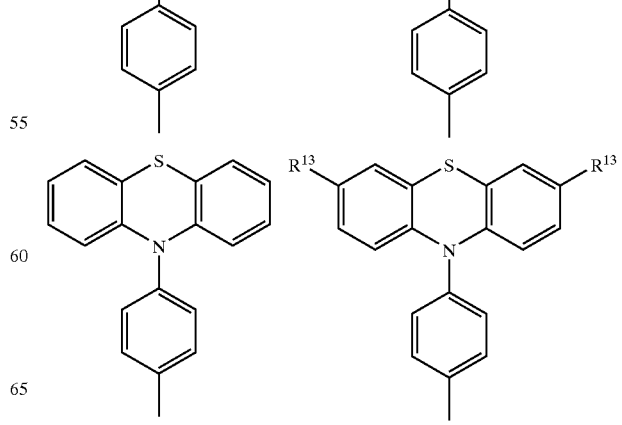

-continued

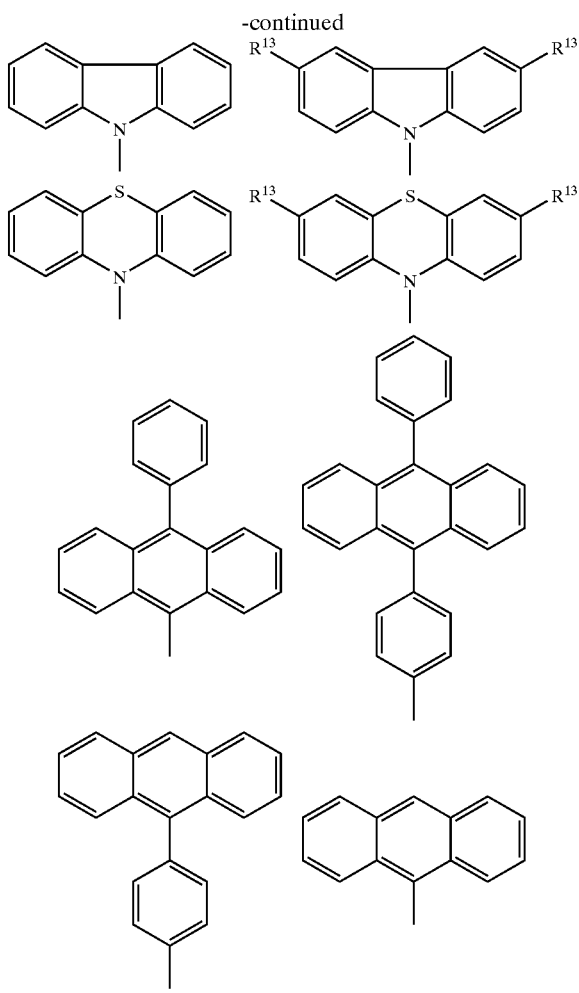

and Q=H and $P^1$ is selected from the group consisting of:

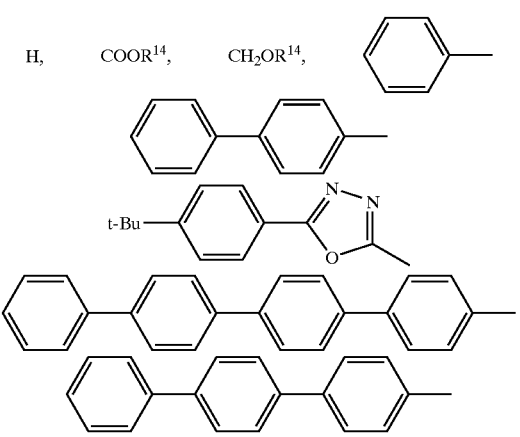

where $R^{13}$, $R^{14}$ are as defined above.

The preparation of the spiro compounds of the invention is carried out by methods known per se from the literature, as are described in standard works on organic synthesis, e.g. Houben-Weyl, Methoden der Organischen Chemie, Georg-Thieme-Verlag, Stuttgart and in the appropriate volumes of the series "The Chemistry of Heterocyclic Compounds" by A. Weissberger and E. C. Taylor (editors).

The preparation is carried out under reaction conditions which are known and suitable for the reactions mentioned. Use can also be made of variants which are known per se and are not mentioned in more detail here.

Compounds of the formula (I) are obtained, for example, starting from 9,9'-spirobifluorene, whose synthesis is described, for example, by R. G. Clarkson, M. Gomberg, J. Am. Chem. Soc. 1030, 52, 2881.

The preparation of compounds of the formula (IIa) can be carried out, for example, starting with a tetrahalogenation in the 2,2',7,7' positions of 9,9'-spirobifluorene and a subsequent substitution reaction (see, for example, U.S. Pat. No. 5,026,894) or via a tetraacetylation of the 2,2',7,7' positions of 9,9'-spirobifluorene with subsequent C—C coupling after conversion of the acetyl groups into aldehyde groups or heterocycle formation after conversion of the acetyl groups into carboxylic acid groups.

The preparation of compounds of the formula (IIb) can be carried out, for example, by methods analogous to those for the formula (IIa) with the stoichiometric ratios in the reaction being selected so that the 2,2' or 7,7' positions are functionalized (see, for example, J. H. Weisburger, E. K. Weisburger, F. E. Ray, J. Am. Chem. Soc. 1959, 72 4253; F. K. Sutcliffe, H. M. Shahidi, D. Paterson, J. Soc. Dyers Colour 1978, 94, 306 and G. Haas, V. Prelog, Helv. Chim. Acta 1969, 52, 1202).

The preparation of compounds of the formula (IIc) can be carried out, for example, via a dibromination in the 2,2' positions and subsequent diacetylation in the 7,7' positions of 9,9'-spirobifluorene with subsequent reaction similar to that for the compounds (IIc).

Compounds of the formulae (II) in which $K^1$, L, Q, $P^1$=H and M=$N^1$ or Q, $P^1$=H, $K^1$=L and M=$N^1$ can be prepared, for example, by choice of appropriately substituted starting compounds in the formation of the spirobifluorene, e.g. 2,7-dibromospirobifluorene can be built up from 2,7-dibromofluorenone and 2,7-dicarbethoxy-9,9'-spirobifluorene by use of 2,7-dicarbethoxyfluorenone. The free 2',7' positions of the spirobifluorene can then be further substituted independently.

For the synthesis of the groups $K^1$, L, M, $N^1$, $P^1$, $R^1$, $R^2$, $R^3$, $R^4$, reference may be made, for example, to DE-A 23 44 732, 24 50 088, 24 29 093, 25 02 904, 26 36 684, 27 01 591 and 27 52 975 for compounds having 1,4-phenylene groups; DE-A 26 41 724 for compounds having pyrimidine-2,5-diyl groups; DE-A 40 26 223 and EP-A 0 391 203 for compounds having pyridine-2,5-diyl groups; DE-A 32 31 462 for compounds having pyridazine-3,6-diyl groups; N. Miyaura, T. Yanagi and A Suzuki in Synthetic Communications 1981, 11, 513 to 519, DE-A 39 30 663; M. J. Sharp, W. Cheng, V. Snieckus, Tetrahedron Letters 1987, 28, 5093; G. W. Gray, J. Chem. Soc. Perkin Trans II 1989, 2041 and Mol Cryst. Liq. Cryst. 1989,172, 165; Mol. Cryst. Liq. Cryst. 1991, 204, 43 and 91; EP-A 0 449 015; WO 89/12039; WO 89/03821; EP-A 0 354 434 for the direct coupling of aromatics and heteroaromatics.

The preparation of disubstituted pyridines, disubstituted pyrazines, disubstituted pyrimidines and disubstituted pyridazines is described, for example, in the appropriate volumes of the series "The Chemistry of Heterocyclic Compounds" by A. Weissberger and E. C. Taylor (editors).

Amino compounds of the formula (I) can be built up by means of variants of the Ullmann reaction (J. March, Adv. Org. Chem., 4$^{th}$ edition, p. 665, John Wiley & Sons, New York 1992), as is described, for example, in Chem. Lett. 1989, p. 1145; Mol. Cryst. Liq. Cryst. 1994, 242, 127 and particularly in J. Salbeck et al., 213$^{th}$ ACS National Meeting, San Francisco 1997, Book of Abstracts p. 199. A further possibility is a process known from U.S. Pat. No. 5,576,460. Preference is given to preparing such compounds by a process disclosed in the German patent application 19738860.4 having the title "Verfahren zur Herstellung von Aryloligoaminen". This application is expressly incorporated by reference into the present description.

The novel spiro compounds of the formula (I) are suitable as charge transport materials, preferably for photovoltaic cells.

The invention therefore also provides for the use of spiro compounds of the formula (I) as charge transport material, in particular for photovoltaic cells.

The invention further provides a photovoltaic cell having a charge transport layer which comprises, preferably consists of, one or more, preferably one, Spiro compound of the formula (I).

FIG. 1 shows a preferred embodiment of such a cell 1 (not to scale).

A conductive support 11, which can serve as electrode or contact and comprises, for example, a metal or indium-tin oxide (ITO), has applied to it, as light-absorbing layer, a semiconductor 12 which preferably has a surface having a roughness factor of >1. The cell of the invention preferably has a chromophore layer 13, on the surface of the semiconductor. For the purposes of the present invention, the term light-absorbing layer encompasses both a semiconductor layer and a combination semiconductor/chromophore, even if the chromophore is in this case almost entirely responsible for the actual absorption. This is adjoined by the charge transport layer 14 which, according to the invention, comprises a Spiro compound of the formula (I). It is bounded on one side by the counterelectrode 15 which can comprise, for example, a conductive glass, conductively coated plastic, metal or another conductive, preferably translucent, material. The cell 1 is preferably closed at the top and bottom by insulating layers 16 and 17. It can comprise a lateral closure not shown in the figure, for example a frame of electrically insulating material such as plastic or glass. However, the use of a hole conductor material in place of the liquid electrolyte makes such a lateral frame unnecessary in principle. At least one side of the cell has to be translucent so that the light to be converted into electric energy can reach the chromophore or the semiconductor. In addition, the cell comprises devices not shown in the figure for taking off the electric current generated by the cell.

The photovoltaic cell of the invention preferably comprises, as light-absorbing layer, a semiconductor which preferably has a very large band gap, particularly preferably at least 3.0 eV, very particularly preferably above 3.0 eV.

As semiconductors, preference is given to metal oxide semiconductors, in particular the oxides of the transition metals and also of the elements of main group III and transition groups IV, V and VI (of the Periodic Table of the Elements), of titanium, zirconium, hafnium, strontium, zinc, indium, yttrium, lanthanum, vanadium, niobium, tantalum, chromium, molybdenum, tungsten, but also oxides of zinc, iron, nickel or silver, perovskites such as $SrTiO_3$, $CaTiO_3$, or oxides of other metals of main groups II and III or mixed oxides or oxide mixtures of these metals. However, it is also possible to use any other metal oxide having semiconducting properties and a large energy difference (band gap) between valence band and conduction band. Titanium dioxide is particularly preferred as semiconductor material.

The semiconductor preferably has a roughness factor of greater than 1, particularly preferably greater than 20, very particularly preferably greater than 150. The roughness factor is defined as the ratio of an actual/effective surface area to the area of projection of this surface of a body, in this case the surface of the semiconductor.

The roughness factor can be determined, for example, by gravimetric adsorption methods, as is described, for example, in F. Kohlrausch, Praktische Physik, Volume 1, p. 397 (Stuttgart: B. G. Teubner, 1985). In general, the size of the pores is 5–200 nm, preferably 10–50 nm.

A process for preparing polycrystalline metal oxide semiconductor layers using the sol-gel method (described in detail in, for example, Staider and Augustynski, J. Electrochem. Soc. 1979, 126, 2007) where, in the process step of the hydrolysis of the metal alkoxide, the percentage relative humidity of the surrounding atmosphere can be in a range from 30% to 80% and is kept constant within ±5%, preferably ±1%, gives metal oxide semiconductor layers by means of which a particularly high electric yield can be achieved in photovoltaic cells according to the invention. The rough surface with a polycrystalline structure provides an area increased by the roughness factor for a preferably monomolecular surface layer of a chromophore. As a result, light incident on an area of particular size is converted into electric energy at a significantly higher yield. The semiconductor may be regarded as transparent to the incident light. However, light is partly reflected on the surface and some of it reaches adjacent surfaces. The light which penetrates into the semiconductor and is not absorbed or converted impinges, partly directly and partly indirectly and also partly indirectly after total reflection at the surface, on chromophore molecules on the exit side, as a result of which a significantly higher light yield can be achieved.

The sensitivity, i.e. the photoelectronic yield for visible light, thus also for sunlight, can therefore be increased by chromophores, also referred to as sensitizers or dyes, as charge carriers being chemically bound on or in the surface of the semiconductor (chemisorbed). The two functions of light absorption and charge carrier separation are separated in these photoelectronic systems. The light absorption is performed by the chromophore in the surface region and the separation of the charge carriers occurs at the semiconductor/chromophore interface.

Different chromophores have different spectral sensitivities. The choice of chromophore can thus be matched to the spectral composition of the light from the light source in order to increase the yield as much as possible. Suitable chromophores, i.e. sensitizers, are, in particular, the complexes of transition metals of the type metal($L_3$), metal($L_2$) of ruthenium and osmium (e.g. ruthenium-tris(2,2'-bipyridyl-4,4'-dicarboxylic acid) and their salts, ruthenium cis diaqua bipyridyl complexes such as ruthenium cis-diaqua bis(2,2'-bipyridyl-4,4'-dicarboxylates) and also porphyrins (e.g. zinc tetra(4-carboxyphenyl)porphyrin) and cyanides (e.g. iron hexacyanide complexes) and phthalocyanines.

The chromophores can be chemisorbed, adsorbed or otherwise fixed in the region of the surface of the metal oxide semiconductor. Good results have been achieved, for example, using chromophores which are bound by means of carboxylic acid or phosphonic acid ligands to the surface of the metal oxide semiconductor.

Suitable chromophores are described, for example, in Chem. Rev. 1995, 49–68.

Particular preference is given to ruthenium-tris(2,2'-bipyridyl-4,4'-dicarboxylic acid), its salts and the chromophores (VIII) and (IX),

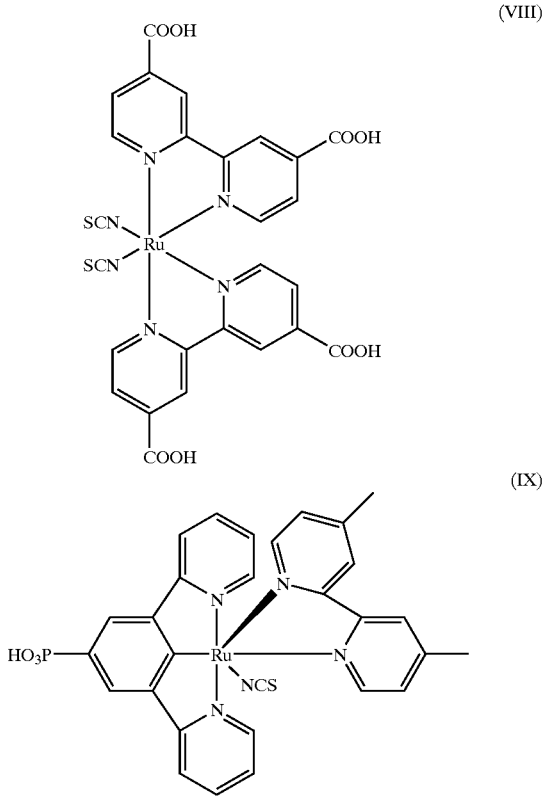

whose synthesis and properties are described in J. Chem. Soc. Chem. Comm. 1995, 65.

The application of the chromophore, for example ruthenium-tris(2,2'-bipyridyl-4,4'-dicarboxylic acid) or a salt thereof, is carried out, for example, by dipping the substrate with the oxide layer into a solution, for example an aqueous or alcoholic, preferably ethanolic, solution, for about one hour. The concentration of the solution is preferably from 0.1 to 10 molar, particularly preferably from 1 to 5 molar, for example 2 molar. Other chromophores can be applied to titanium oxide or other metal oxide semiconductors by analogous methods.

Materials suitable as electrode 15 are stable, metallically conductive substances, e.g. Au, Ag, Pt, Cu or other metals. However, for some applications it is also possible to use preferably translucent conductive substances such as doped metal oxides, e.g. indium-tin oxide, Sb-doped tin oxide or Al-doped zinc oxide. The work function of the electrode material used is preferably matched to the ionization potential of the hole transport material employed.

The electrode can, as described in EP-A 0 333 641, be applied to a transparent substrate, e.g. glass, and joined to the hole transport layer. In the cell of the invention, it is preferably applied directly to the hole transport layer by physical deposition methods, e.g. vapor deposition or sputtering, without a second glass plate being necessary. This process is preferred in applications in which the weight of the cell is to be reduced.

If desired, the cell can be sealed, e.g. by means of an adhesive or a film.

A photovoltaic cell according to the invention generally has a thickness of from 5 to 20 mm (including substrate).

To avoid reflection losses, it can be provided with a single-layer, two-layer or multilayer antireflection coating.

Spiro compounds of the formula (I) are also suitable as electroluminescence materials.

For the purposes of the present invention, electroluminescence materials are materials which are used as active layer in an electroluminescence device. Active layer means that the layer is capable of emitting light on application of an electric field (light-emitting layer) and/or that it improves the injection and/or transport of positive and/or negative charges (charge injection or charge transport layer).

The invention therefore also provides for the use of a spiro compound of the formula (I) as electroluminescence material, i.e. use as active layer in an electroluminescence device.

To be used as electroluminescence materials, the spiro compounds of the formula (I) are applied in the form of a film to a substrate, generally by known methods with which those skilled in the art are familiar, e.g. dipping or spin-coating.

The invention further provides an electroluminescence device having one or more active layers of which at least one comprises one or more novel spiro compounds of the formula (I). The active layer can, for example, be a light-emitting layer and/or a transport layer and/or a charge injection layer.

The general structure of such electroluminescence devices is described, for example, in U.S. Pat. Nos. 4,539,507 and 5,151,629. Polymer-containing electroluminescence devices are described, for example, in WO-A 90/13148 or EP-A 0 443 861.

They customarily comprise an electroluminescent layer between a cathode and an anode, with at least one of the electrodes being transparent. In addition, one or more electron injection and/or electron transport layers can be inserted between the electroluminescent layer and the cathode and/or one or more hole injection and/or hole transport layers can be inserted between the electroluminescent layer and the anode. Materials employed for the cathode are preferably metals or metallic alloys, e.g. Ca, Mg, Al, In, Mg/Ag. Materials used as anode are, for example, metals, e.g. Au, or other metallically conductive materials such as oxides, e.g. ITO (indium oxide/tin oxide) on a transparent substrate, e.g. of glass or a transparent polymer.

In operation, the cathode is placed at a negative potential relative to the anode. As a result, electrons from the cathode are injected into the electron injection layer/electron transport layer or directly into the light-emitting layer. At the same time, holes from the anode are injected into the hole injection layer/hole transport layer or directly into the light-emitting layer.

The injected charge carriers move toward one another through the active layers under the action of the applied potential. This leads to electron/hole pairs at the interface between charge transport layer and light-emitting layer or within the light-emitting layer and these pairs recombine with emission of light. The color of the emitted light can be varied by means of the materials used as light-emitting layer.

Electroluminescence devices are employed, for example, as self-illuminating display elements such as indicator lamps, alphanumeric displays, signs, and in optoelectronic couplers.

The contents of the German patent application 19711714.7 having the title "Spiroverbindungen und deren Verwendung", on which the priority of the present application is based, and also the contents of the abstract of the present application are hereby expressly incorporated by reference into the present application.

The invention is illustrated by the examples, without being restricted thereby.

EXAMPLES

A. Starting Compounds a) 9,9'-Spirobifluorene 6.3 g of magnesium turnings and 50 mg of anthracene were placed in 120 ml of dry diethyl ether under argon in a 1 l three-necked flasked fitted with reflux condenser and the magnesium was activated by means of ultrasound for 15 minutes.

62 g of 2-bromobiphenyl were dissolved in 60 ml of dry diethyl ether. About 10 ml of this solution were added to the initially-charged magnesium in order to start the Grignard reaction.

After the reaction had started, while continuing to treat with ultrasound, the 2-bromobiphenyl solution was added dropwise at such a rate that the solution refluxed gently. After addition was complete, the reaction mixture was refluxed under ultrasound for a further hour.

48.8 g of 9-fluorenone were dissolved in 400 ml of dry diethyl ether and, while continuing to treat with ultrasound, added dropwise to the Grignard solution. After addition was complete, the mixture was boiled for another 2 hours. The yellow magnesium complex of 9-(2-biphenyl)-9-fluorenol which precipitated after cooling the reaction mixture was filtered off with suction and washed with a little ether. The magnesium complex is hydrolyzed in 800 ml of ice water containing 40 g of ammonium chloride. After stirring for 60 minutes, the 9-(2-biphenyl)-9-fluorenol formed was filtered off with suction, washed with water and sucked dry.

The dried 9-(2-biphenyl)-9-fluorenol was then dissolved in 500 ml of hot glacial acetic acid. 0.5 ml of concentrated HCl was added to this solution. The solution was boiled for a few minutes and the 9,9'-spirobifluorene formed was precipitated from the hot solution by means of water (water added to incipient turbidity). After cooling, the product was filtered off with suction and washed with water. The dried product was purified further by recrystallization from ethanol. This gave 66 g (80%, based on 2-bromobiphenyl) of 9,9'-spirobifluorene as colorless crystals, mp. 198° C.

b) 2,2'-Dibromo-9,9'-spirobifluorene (F. K. Sutcliffe, H. M. Shahidi, D. Patterson, J. Soc. Dyers Colour 94 (1978) 306)

3.26 g (10.3 mmol) of 9,9'-spirobifluorene were dissolved in 30 ml of methylene chloride and admixed with 5 mg of $FeCl_3$ (anhydrous) as catalyst. The reaction flask was protected from light. 1.12 ml (21.8 mmol) of bromine in 5 ml of methylene chloride were added dropwise over a period of 30 minutes while stirring. After 24 hours, the resulting brown solution was washed with saturated $NaHCO_3$ solution and water to remove excess bromine. The organic phase was dried over $Na_2SO_4$ and then evaporated on a rotary evaporator. The white residue was recrystallized from methanol, giving 3.45 g (70%) of the dibromo compound as colorless crystals, mp. 240° C.

c) 2,7-Dibromo-9,9'-spirobifluorene

A Grignard reagent prepared from 0.72 g (30 mmol) of magnesium turnings and 5.1 ml (30 mmol) of 2-bromobiphenyl in 15 ml of diethyl ether was added dropwise while stirring (in an ultrasonic bath) to a boiling suspension of 10.0 g (29.6 mmol) of 2,7-dibromo-9-fluorenone in 100 ml of dry diethyl ether over a period of 2 hours. After addition was complete, the mixture was boiled for a further 3 hours. After cooling overnight, the precipitate formed was filtered off with suction and washed with cold ether. The magnesium complex which had been filtered off with suction was hydrolyzed in a solution of 15 g of ammonium chloride in 250 ml of ice water. After 1 hour, the 9-(2-biphenylyl)-2,7-dibromo-9-fluorenol formed was filtered off with suction, washed with water and sucked dry. For the ring closure reaction, the dried fluorenol was boiled in 100 ml of glacial acetic acid, after addition of 3 drops of concentrated HCl, for 6 hours. The mixture was allowed to crystallize overnight, the product formed was filtered off with suction and washed with glacial acetic acid and water.

Yield: 11 g (77%) of 2,7-dibromo-9,9'-spirobifluorene. This was purified further by recrystallization from THF.
$^1$H-NMR ($CDCl_3$, ppm): 6.73 (d, J=7.63 Hz, 2 H, H-1',8'); 6.84 (d, J=1.83 Hz, 2 H, H-1,8); 7.15 (td, J=7.63, 1.22 Hz, 2 H, H-2',7'); 7.41 (td, J=7.63, 1.22 Hz, 2 H, H-3',6'); 7.48 (dd, J=8.24, 1.83 Hz, 2 H, H-3,6); 7.67 (d, J=8.24; 2 H; H-4,5); 7.85 (d, J=7.63, 2 H, H-4',5').

d) 2,2',7,7'-Tetrabromo-9,9'-spirobifluorene 80 mg (0.5 mmol) of anhydrous $FeCl_3$ were added to a solution of 3.16 g (10.0 mmol) of 9,9'-spirobifluorene in 30 ml of methylene chloride, and 2.1 ml (41 mmol) of bromine in 5 ml of methylene chloride were added dropwise over a period of 10 minutes. The solution was refluxed for 6 hours. On cooling, the product precipitated. The precipitate was filtered off with suction and washed with a little cold methylene chloride. Drying gave 6.0 g (95%) of the tetrabromo compound as a white solid.

e) 2-Bromo-9,9'-spirobifluorene and 2,2',7-tribromo-9,9'-spirobifluorene can be prepared in an analogous way using a different stoichiometry.

f) 2,2',4,4',7,7'-Hexabromo-9,9'-spirobifluorene

In a 250 ml three-necked flask fitted with drying tube and dropping funnel, 6.43 ml of bromine in 10 ml of methylene chloride were added at room temperature while stirring to a solution of 6.32 g of 9,9'-spirobifluorene in 40 ml of methylene chloride (together with a spatula tip of anhydrous $FeCl_3$) over a period of 10 minutes in the absence of light. After 1 hour, the white precipitate formed was filtered off with suction. Solid and mother liquor were worked up separately. The solid was dissolved in $CH_2Cl_2$ and, like the mother liquor, washed with saturated $Na_2SO_3$ solution, saturated $NaHCO_3$ solution and water, dried over $Na_2SO_4$ and evaporated. 10.0 g of pure, colorless 2,2',4,4',7,7'-hexabromo-9,9'-spirobifluorene were isolated from the solid fraction and another 5.7 g of slightly colored product could be isolated from the mother liquor. The total yield was almost quantitative.

g) 2,2',7,7'-Tetraiodo-9,9'-spirobifluorene

In a 100 ml two-necked flask fitted with reflux condenser and drying tube, 3.16 g (10 mmol) of 9,9'-spirobifluorene dissolved in 30 ml of chloroform were admixed at room temperature with 5.8 g (22.8 mmol) of iodine and, subsequently, 10.75 g (25 mmol) of bis(trifluoroacetoxy)iodobenzene were added. The reaction mixture heated spontaneously to about 40° C. with formation of a light-colored precipitate. After 1.5 hours, the product which had precipitated was filtered off with suction and was washed with chloroform and dried. The chloroform solutions are combined and washed in succession with saturated sodium sulfite solution, saturated sodium carbonate solution and water. After drying over sodium sulfate, the solution was evaporated and a second product fraction was obtained. Both product fractions were combined, boiled in acetone, cooled and filtered off with suction. This gave 2,2',7,7'-tetraiodo-9,9'-spirobifluorene as a finely crystalline colorless powder in virtually quantitative yield (8.1 g).

¹H-NMR (CDCl₃, ppm): 6.98 (d, J=1.48 Hz, 4 H, H-1, 1',8,8'); 7.54 (dd, J=7.88, 1.48 Hz, 4 H, H-3,3',6,6'); 7.72 (d, J=7.88 Hz, 4H, H-4,4',5,5').

h) 9,9'-Spirobifluorene-2,2'-dicarboxylic acid
from 2,2'-dibromo-9,9'-spirobifluorene via 2,2'-dicyano-9,9'-spirobifluorene. 1.19 g of 2,2'-dibromo-9,9'-spirobifluorene and 0.54 g of CuCN were heated under reflux in 5 ml of DMF for 6 hours. The brown mixture obtained was poured into a mixture of 3 g of FeCl₃ (hydrated) and 1.5 ml of concentrated HCl in 20 ml of water. The mixture was held at from 60 to 70° C. for 30 minutes in order to destroy the Cu complex. The hot aqueous solution was extracted twice with toluene. The organic phases were then washed with dilute HCl, water and 10% strength NaOH. The organic phase was filtered and evaporated. The yellow residue obtained was recrystallized from methanol, giving 0.72 g (80%) of 2,2'-dicyano-9,9'-spirobifluorene as slightly yellowish crystals (melting range: 215–145° C.).

3 g of 2,2'-dicyano-9,9'-spirobifluorene were refluxed with 25 ml of 30% strength NaOH and 30 ml of ethanol for 6 hours. The disodium salt of spirobifluorenedicarboxylic acid was precipitated as a yellow solid which was filtered off and heated in 25% strength HCl in order to isolate the free acid. The spirobifluorenedicarboxylic acid was recrystallized from glacial acetic acid. This gave 2.2 g (66.6%) of white crystals (mp. 376° C., IR band: 1685 cm⁻¹ C=O).

i–k) 9,9'-Spirobifluorene-2,2',7,7'-tetracarboxylic acid can be prepared in an analogous way from 2,2',7,7'-tetrabromo-9,9'-spirobifluorene; likewise, 9,9'-spirobifluorene-2,2',7-tricarboxylic acid can be prepared from 2,2',7-tribromo-9,9'-spirobifluorene and 9,9'-spirobifluorene-2,2',4,4',7,7'-hexacarboxylic acid can be prepared from 2,2',4,4',7,7'-hexabromo-9,9'-spirobifluorene by analogous methods.

l) 9,9'-Spirobifluorene-2,2'-dicarboxylic acid
from 9,9'-spirobifluorene via 2,2'-diacetyl-9,9'-spirobifluorene (G. Haas, V. Prelog, Heiv. Chim. Acta 52 (1969) 1202; V. Prelog. D. Bedekovic, Helv. Chim. Acta 62 (1979) 2285)
9.0 g of finely powdered, anhydrous AlCl₃ were added to a solution of 3.17 g of 9,9'-spirobifluorene in 30 ml of absolute carbon disulfide and, while stirring, 1.58 g of acetyl chloride in 5 ml of absolute carbon disulfide were then added dropwise over a period of 10 minutes and the mixture was refluxed for 1 hour. The mixture was evaporated to dryness under reduced pressure and then admixed at 0° C. with 100 g of ice and 50 ml of 2N hydrochloric acid. After a customary work-up, the crude product was fractionated chromatographically on silica gel by means of benzene/ethyl acetate (10:1). This gave 3.62 g (89%) of 2,2'-diacetyl-9,9'-spirobifluorene (recrystallized from chloroform/ethyl acetate, mp. 255–257° C. ) and 204 mg of 2-acetyl-9,9'-spirobifluorene (recrystallized from chloroform/benzene, mp. 225° C.).

[in addition, the chromatography also enabled isolation of 2,2',7-triacetyl-9,9'-spirobifluorene (mp. 258–260° C.) and 2,2',7,7'-tetraacetyl-9,9'-spirobifluorene (mp. >300° C.), recrystallized from ethyl acetate/hexane].

While stirring. first 7.2 g of bromine and then a solution of 3.0 g of 2,2'-diacetyl-9,9'-spirobifluorene in a little dioxane were added dropwise at 0° C. to a solution of 6.0 g of sodium hydroxide in 30 ml of water. After stirring for a further hour at room temperature, the clear yellow solution was admixed with 1 g of sodium hydrogen sulfite dissolved in 20 ml of water. After acidification with concentrated HCl, the colorless product which precipitated was filtered off and washed with a little water. Recrystallization from ethanol gave 9,9'-spirobifluorene-2,2'-dicarboxylic acid as clear, colorless prisms (mp. 352° C.).

m) Synthesis of 2,7-dicarbethoxy-9,9'-spirobifluorene
A Grignard reagent prepared from 0.97 g (40 mmol) of magnesium turnings and 9.32 g (6.8 ml, 40 mmol) of 2-bromobiphenyl in 50 ml of dry diethyl ether was added dropwise to a boiling solution of 13 g (40 mmol) of 2,7-dicarbethoxy-9-fluorenone in 100 ml of dry diethyl ether over a period of 2 hours. After addition was complete, the mixture was boiled for a further 3 hours. After cooling overnight, the precipitate formed was filtered off with suction and washed with cold ether. The magnesium complex which had been filtered off with suction was hydrolyzed in a solution of 15 g of ammonium chloride in 250 ml of ice water. After 1 hour, the 9-(2-biphenylyl)-2,7-dicarbethoxy-9-fluorenol formed was filtered off with suction, washed with water and sucked dry. For the ring closure reaction, the dried fluorenol was boiled in 100 ml of glacial acetic acid, after addition of 3 drops of concentrated HCl, for 6 hours. The mixture was allowed to crystallize overnight, the product formed was filtered off with suction and was washed with glacial acetic acid and water.

Yield: 15.1 g (82%) of 2,7-dicarbethoxy-9,9'-spirobifluorene. The product was purified further by recrystallization from ethanol. ¹H-NMR (CDCl₃, ppm): 1.30 (t, J=Hz, 6 H, ester-CH₃); 4.27 (q, J=Hz, 4 H, ester-CH₃); 6.68 (dt, J=7.63, 0.92 Hz, 2 H, H-1',8'); 7.11 (td, J=7.48, 1.22 Hz, 2H, H-2',7'); 7.40 (td, J=7.48, 1.22 Hz, 4 H, H-1,8,3',6'); 7.89 (dt, J=7.63, 0.92 Hz, 2 H, H-4',5'); 7.94 (dd, J=7.93, 0.6 Hz, 2 H, H-4,5); 8.12 (dd J=7.93, 1.53 Hz, 2 H, H-3,6).

n) Spirobifluorene-4-carboxylic acid
In a 2 l flask, 100 g of fluorenone were dissolved in 1000 ml of dry xylene and admixed while stirring with 200 g of dry NaOH. The mixture was subsequently refluxed for 70 hours. After cooling, the mixture was filtered with suction and the residue was admixed with about 2 l of water. The aqueous suspension was filtered with suction and the precipitate was again slurried with toluene, filtered off with suction and dried. This intermediate was dissolved using about 5 ml of glacial acetic acid per 1 g by refluxing in a 500 ml two-necked flask fitted with reflux condenser and drying tube, 20 ml of concentrated HCl were added and the mixture was refluxed for 5 hours. The reaction mixture was evaporated to about half its volume and was subsequently poured into four times its volume of H₂O. The precipitate formed was filtered off with suction, washed well with H₂O and dried. To purify it further, it was dissolved at room temperature in an alkaline MeOH/water (10:1) mixture and shaken with toluene. The MeOH/water phase was separated off and, after acidification with hydrochloric acid, poured into water. The spirobifluorene-4-carboxylic acid which was precipitated was filtered off with suction, washed with water and dried. Yield: 35 g.

o) 2',7'-Dibromo-9,9'-spirobifluorene-4-carboxylic acid
60 g of 9,9'-spirobifluorene-4-carboxylic acid were dissolved in 600 ml of hot chloroform and admixed with 1 spatula tip of iron(III) chloride. 60 ml of bromine in 60 ml of CHCl₃ were added dropwise via a dropping funnel over a period of 30 minutes and the mixture was refluxed for a further 90 minutes. After cooling, the precipitate formed was filtered off with suction and washed, the filtrate was washed with Na₂SO₃ solution and NaHCO₃ solution and water. After work-up and purification by a method similar to that for the hexabromination, 74.3 g (85%) of 2',7'-dibromo-9,9'-spirobifluorene-4-carboxylic acid were isolated as a white powder.

p) 2,2'-Bis(bromomethyl)-9,9'-spirobifluorene from 2,2'-dicarboxy-9,9'-spirobifluorene via 9,9'-spirobifluorene-2,2'-dimethanol (V. Prelog, D. Bedekovic, Helv. Chim. Acta 62 (1979) 2285)

At room temperature, 10 g of a 70% strength solution of sodium dihydrobis(2-methoxyethoxy)aluminate (Fluka) in benzene were slowly added dropwise to a suspension of 2.0 g of 2,2'-dicarboxy-9,9'-spirobifluorene (free carboxylic acid) in 20 ml of benzene. After refluxing for 2 hours, during which time the carboxylic acid dissolved, the excess reducing agent was decomposed at 10° C. by means of water, the mixture was acidified with concentrated HCl and shaken with chloroform.

The organic phase was washed with water and dried over magnesium sulfate, evaporated and the residue was recrystallized from benzene. This gave 1.57 g of 9,9'-spirobifluorene-2,2'-dimethanol (mp. 254–255° C.).

91.5 g of a 33% strength solution of hydrogen bromide in glacial acetic acid were added dropwise to a solution of 13.5 g of 9,9'-spirobifluorene-2,2'-dimethanol in 400 ml of benzene and the mixture was refluxed for 7 hours. 200 ml of water were then added and the organic phase was washed with water, dried over magnesium sulfate and evaporated. Chromatography on silica gel using benzene gave 11.7 g of 2,2'-bis(bromomethyl)-9,9'-spirobifluorene as colorless platelets (mp. 175–177° C.).

q) 9,9'-Spirobifluorene-2,2'-dicarbaldehyde and
r) 2'-hydroxymethyl-9,9'-spirobifluorene-2-carbaldehyde.

A solution of 380 mg of 9,9'-spirobifluorene-2,2'-dimethanol in 15 ml of toluene was admixed with 5 g of chromium(VI) oxide on graphite (Seloxcette, Alpha Inorganics) and refluxed under nitrogen for 48 hours. The mixture was then filtered with suction on a glass suction filter and the filtrate was evaporated. Chromatography on silica gel using chloroform and crystallization from methylene chloride/ether gave 152 mg of 9,9'-spirobifluorene-2,2'-dicarbaldehyde (mp. >300° C.) and 204 mg of 2'-hydroxymethyl-9,9'-spirobifluorene-2-carbaldehyde (mp. 262–263° C.).

s) 2,2'-Diamino-9,9'-spirobifluorene

A mixture of 150 ml of concentrated HNO₃ and 150 ml of glacial acetic acid was added dropwise to a boiling solution of 15.1 g of 9,9'-spirobifluorene in 500 ml of glacial acetic acid over a period of 30 minutes and the solution was subsequently refluxed for another 75 minutes. After cooling and allowing the solution to stand for 1 hour, the same volume of water was added, resulting in precipitation of the product. Filtration with suction gave 18.5 g of yellow crystals (mp. 220–224° C.) of 2,2'-dinitro-9,9'-spirobifluorene. Recrystallization from 250 ml of glacial acetic acid gives 12.7 g of light-yellow crystalline needles (mp. 245–249° C., analytically pure: 249–250° C.).

A mixture of 4.0 ml of dinitrospirobifluorene and 4.0 g of iron powder was refluxed in 100 ml of ethanol while 15 ml of concentrated HCl were added dropwise over a period of 30 minutes. After refluxing for a further 30 minutes, excess iron was filtered off. The green filtrate was added to a solution comprising 400 ml of water, 15 ml of concentrated NH₄OH and 20 g of sodium potassium tartrate. The white diamine was filtered off from the dark green solution of the iron complex. To purify the diamine, it was dissolved in dilute HCl, stirred with activated carbon (Darco) at room temperature and filtered. The filtered solution was neutralized by dropwise addition of NH₄OH while stirring (precision glass stirrer) and the precipitated product was filtered off with suction. This gave 3.5 g of white 2,2'-diamino-9,9'-spirobifluorene which was recrystallized from ethanol (mp. 243° C.).

B. Synthesis Examples a) N,N,N', N',N', N", N", N'",N'"-Octakis(4-methoxyphenyl)-9,9'-spirobifluorene-2,2', 7,7'-tetramine The reaction of tetraiodospirobifluorene with 4,4'-dimethoxydiphenylamine using a method analogous to that described above gave a comparable yield of N,N,N', N',N", N", N'", N'"-octakis(4-methoxyphenyl)-9,9'-spirobifluorene-2,2', 7,7'-tetramine as a yellowish crystalline powder.

¹H-NMR (CDCl₃, ppm): 3.76 (s, 24 H, OCH₃); 6.54 (d, J=1.99 Hz, 4 H, H-1,1', 8,8'); 6.75 (dm. J=9.07 Hz, 16 H); 6.79 (dd, J=8.18, 1.99 Hz, 4 H, H-3,3', 6,6'); 6.90 (dm, J=9.07 Hz, 16); 7.35 (d, J=8.18 Hz, 4 H, H-4,4',5,5').

b) 2,2',7,7'-Tetra(N-carbazolyl)-9,9'-spirobifluorene

In a 100 ml three-necked flask fitted with reflux condenser and nitrogen valve, 5.01 g (6.11 mmol) of 2,2',7,7'-tetraiodospirobifluorene were refluxed (144° C.) with 5.30 g (31.7 mmol) of carbazole, 1.52 g (23.9 mmol) of activated copper, 6.60 g (47.8 mmol) of potassium carbonate and 499 mg (1.89 mmol) of 18-crown-6 in 25 ml of o-xylene for 80 hours. The reaction mixture assumed a greenish color during the course of the reaction. After cooling, the mixture was filtered with suction and the residue was boiled with 30 ml of water for 20 minutes. After cooling, the aqueous suspension was filtered with suction and the product was dissolved from the solid residue by means of 140 ml of chloroform with addition of 3 drops of hydrazine hydrate. The mixture was refluxed for 15 minutes, filtered and the residue was washed with 5 ml of chloroform. The chloroform solution was evaporated on a rotary evaporator to give 5.50 g of crude product. A further fraction (0.890 g) was isolated from the filtrate of the reaction solution by evaporating the solution to dryness, stirring the residue with 5 ml of acetone, filtering with suction and washing with acetone. To remove remaining carbazole, the crude product was heated with toluene and subsequently filtered off with suction. Total yield: 4 g (67%) of 2,2',7,7'-tetra(N-carbazolyl)-9,9'-spirobifluorene. This was purified further by recrystallization from chloroform/methanol.

What is claimed is:
1. A spiro compound of the formula (I)

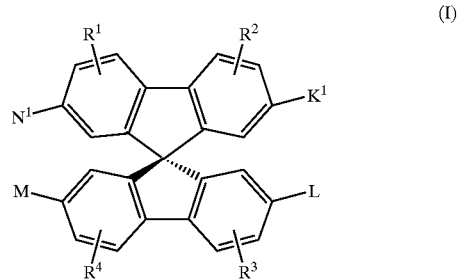

where the symbols have the following meanings:
K¹, L, M, N¹, R¹, R², R³, R⁴ are identical or different and are each a) hydrogen, —NO₂, —CN, —F, or Cl,
b) a straight-chain or branched alkyl radical having from 1 to 20 carbon atoms, where
   b1) one or more nonadjacent CH₂ groups can be replaced by —O—, —S—, —CO—O—, —O—CO—, —O—CO—O—, NR⁵ or —Si(CH₃)₂— and/or
   b2) one or more CH₂ groups can be replaced by —CH=CH—, —C≡C—, 1,4-phenylene, 1,4-cyclohexylene or 1,3-cyclopentylene and/or
   b3) one or more H atoms can be replaced by F and or Cl, and/or
c) one of the following groups:

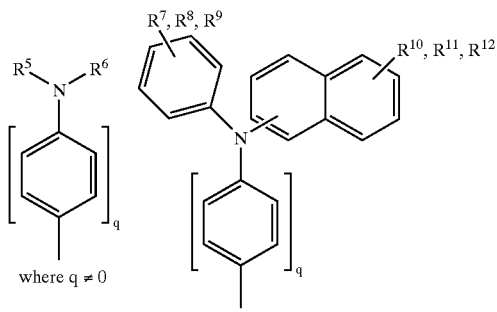

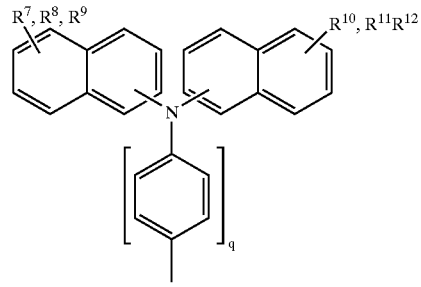

-continued

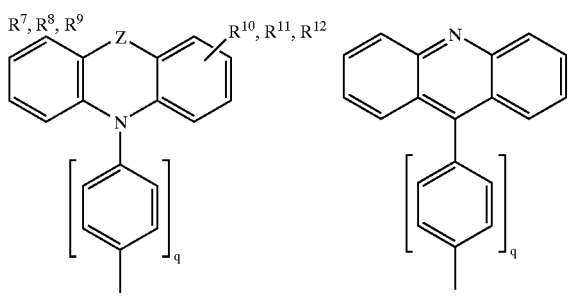

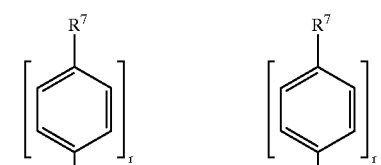

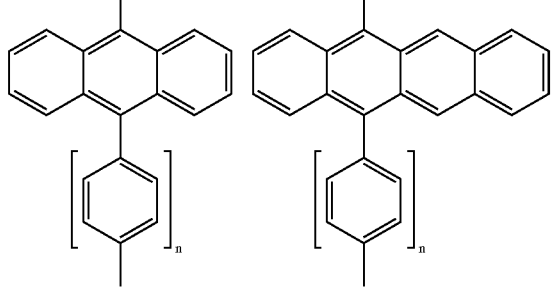

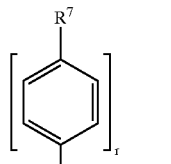

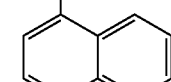

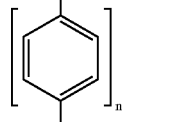

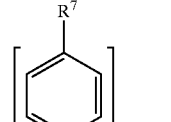

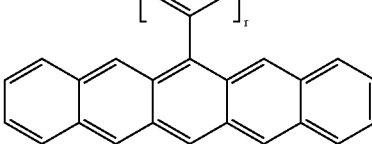

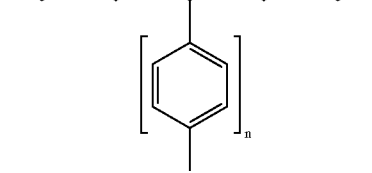

or d) one of the following groups:

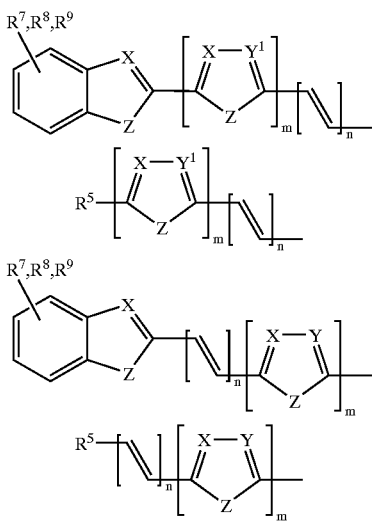

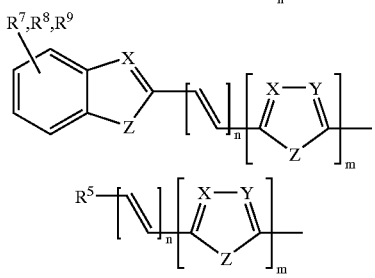

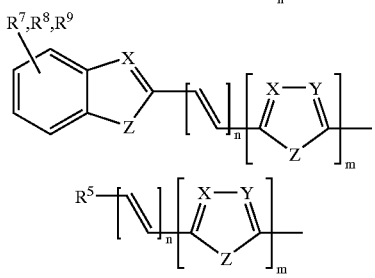

with the proviso that at least one of the radicals $K^1$, L, M, $N^1$, $R^1$, $R^2$, $R^3$, $R^4$ is one of the groups listed under c);

X, $Y^1$ are in each case identical or different and are or $=CR^7-$ or $=N-$;

Z is $-O-$, $-S-$, $NR^5$, $-CRR-$, $-CR=CR-$ or $-CR=N-$;

$R^5$, $R^6$ are in each case identical or different and are each
  a) hydrogen,
  b) a straight chain or branched alkyl radical having from 1 to 20 carbon atoms, where
    b1) one or more nonadjacent $CH_2$ groups are not bound to nitrogen can be replaced by $-O-$, $-S-$, $-CO-O-$, $-O-CO-$, $-O-CO-O-$ or $Si(CH_3)_2-$ and/or
    b2) one or more $CH_2$ groups can be replaced by $-CH=CH-$, $-C\equiv C-$, cyclopropane-1,2-diyl, 1,4-phenylene, 1,4-cycloheylene or 1,3-cyclopentylene and/or
    b3) one or more H atoms can be replaced by F and/or Cl and/or
    b4) $R^5$ and $R^6$ together can also form a ring;
  c) phenyl, biphenyl, 1-naphthyl, 2-naphthyl, 2-thienyl, 2-furanyl $R^7$, $R^8$ $R^9$ $R^{10}$ $R^{11}$ $R^{12}$ are identical or different and are each
  a) hydrogen, $-CN$, $-F$, $NO_2$, or $-Cl$,
  b) a straight-chain or branched alkyl radical having from 1 to 20 carbon atoms, where
    b1) one or more nonadjacent $CH_2$ groups can be replaced by $-O-$, $-S-$, $-CO-O-$, $-O-CO-O-$, $NR^5$ or $-Si(CH_3)_2-$ and/or
    b2) one or more $CH_2$ groups can be replaced by $-CH=CH-$, $-C\equiv C-$, cyclopropane-1,2-diyl, 1,4-phenylene, 1,4-cyclohexylene or 1,3-cyclopentylene and/or
    b3) one or more H atoms can be replaced by F and/or Cl;
  c) phenyl, biphenyl, 1-naphthyl, 2-naphthyl, 2-thienyl, 2-furanyl, $-O$-phenyl, $-O$-biphenyl, $-O$-1-naphthyl, $-O$-2-thienyl, $-O$-2-furanyl, m, n, p, q, r are in each case identical or different and are 0, 1, 2, 3, 4, 5, 6.

2. A spiro compound as claimed in claim 1 which is a spirobifluorene derivative of one of the formulae (II) a–c

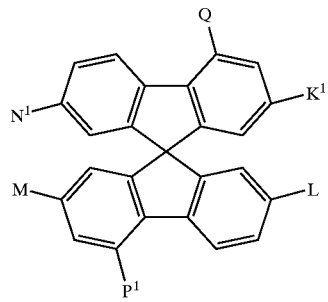

(II)

where the symbols have the following meanings:

II.a) $K^1=L=M=N^1$ and is selected from the group consisting of:

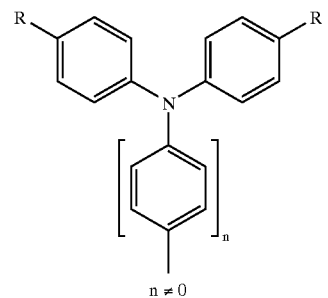

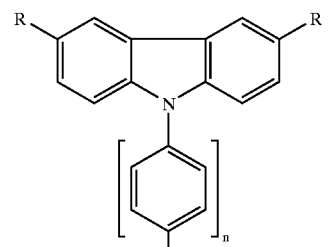

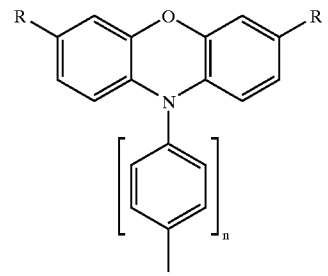

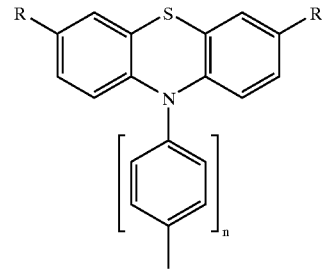

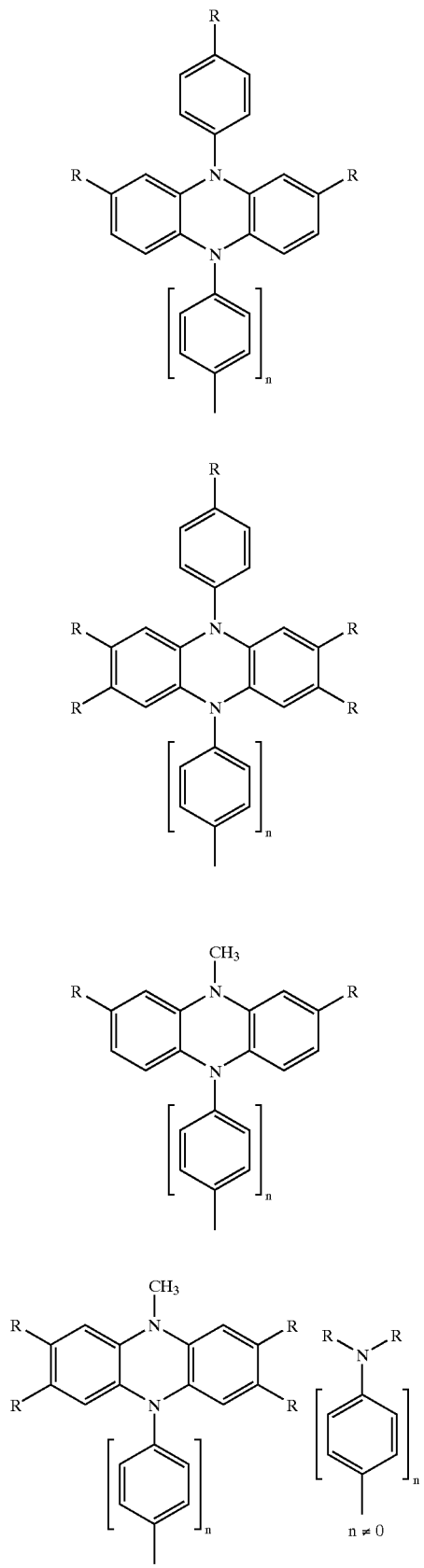
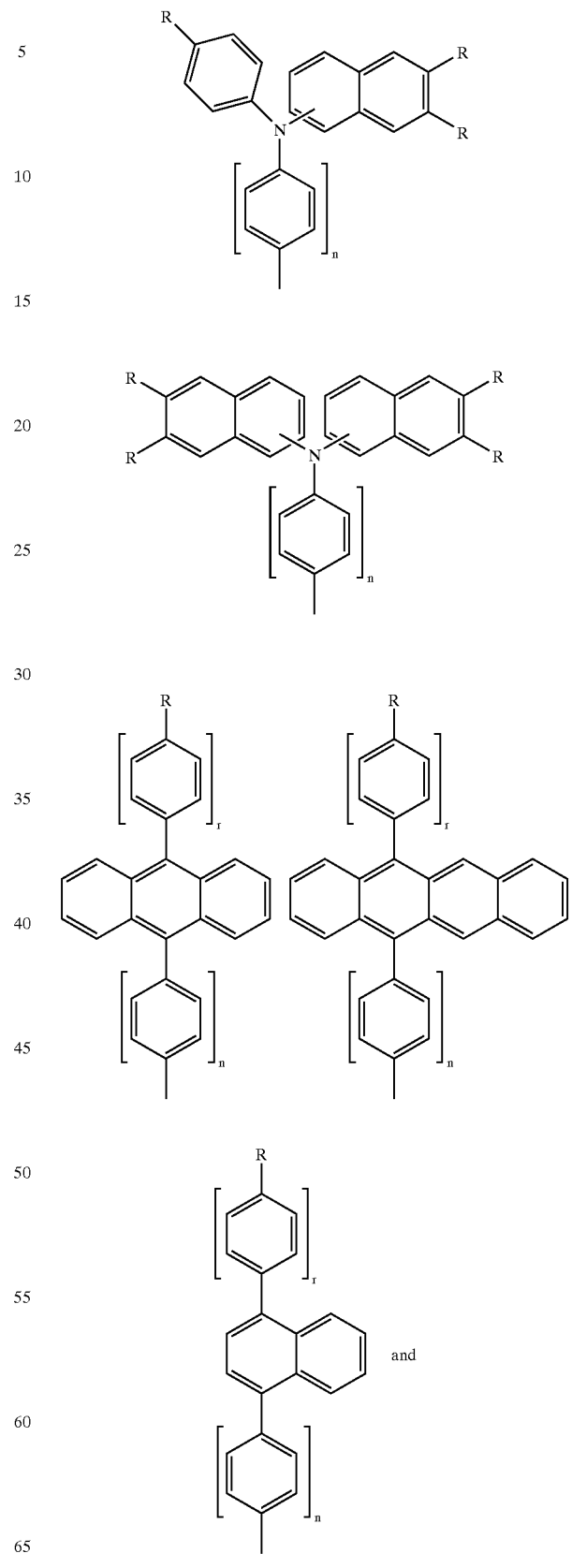

-continued

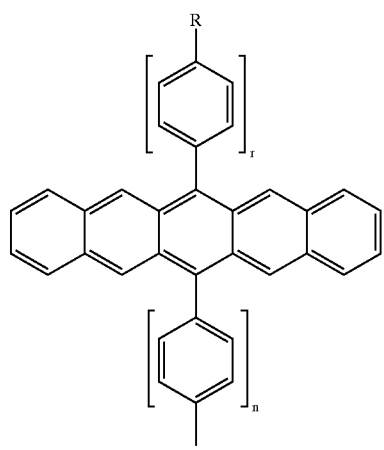

R are identical or different and are H, alkyl, —O-alkyl, —S-alkyl, each having from 1 to 20 carbon atoms, phenyl biphenyl, 1-naphthyl, 2-naphthyl, 2-thienyl, 2-furanyl, O-phenyl, —O-biphenyl, —O-1-naphthyl, —O-2-naphthyl, —O-2-thienyl, —O-2-fumayl, CN, $NR_{2'}$, where —O-alkyl/aryl, —S-alkyl/aryl, CN, $NO_2$ must not be bound to nitrogen;

n=0, 1, 2, 3, 4, and Q, $P^1$ are identical or different and are selected from the group consisting of:

H, COOR, $CH_2OR$,

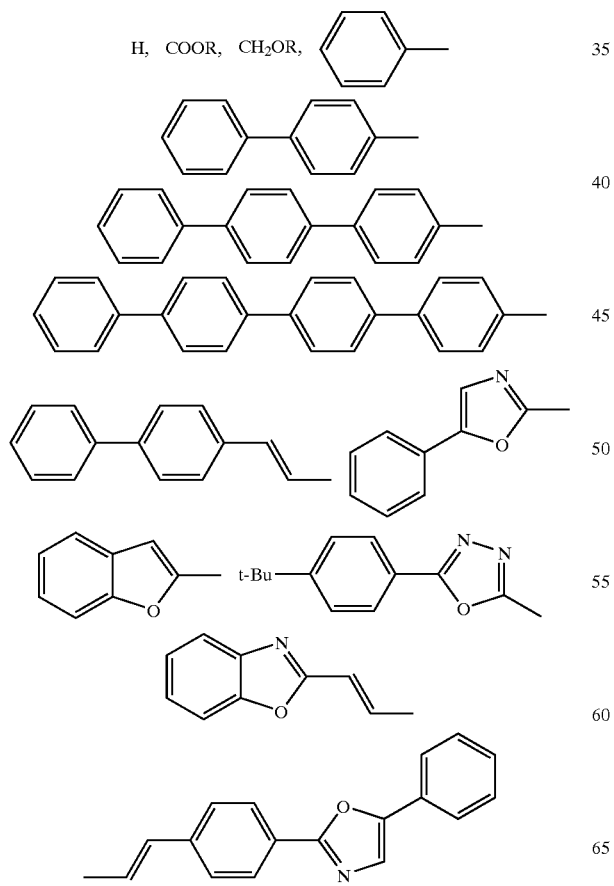

-continued

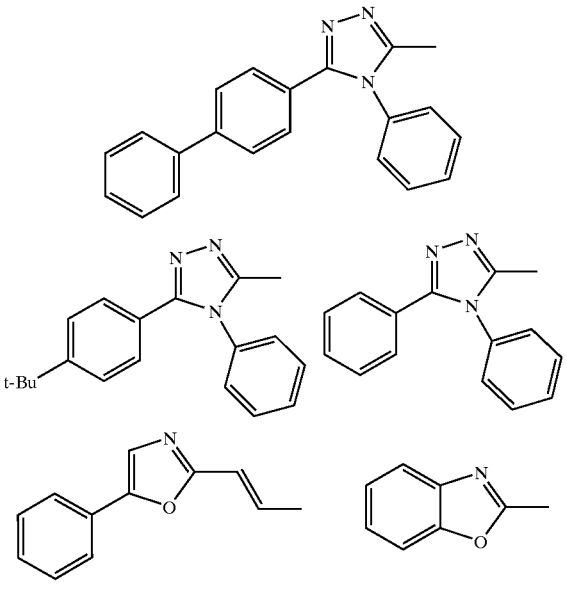

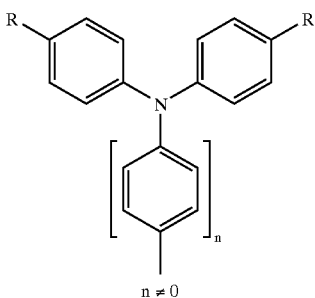

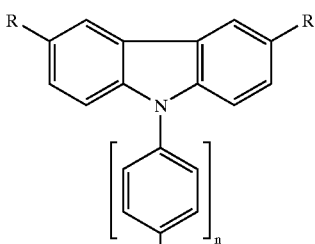

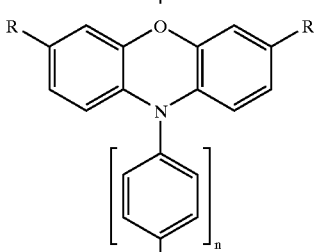

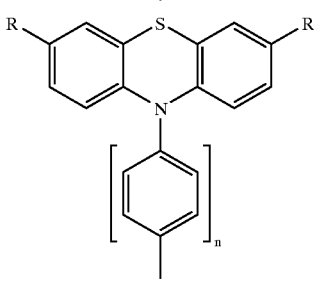

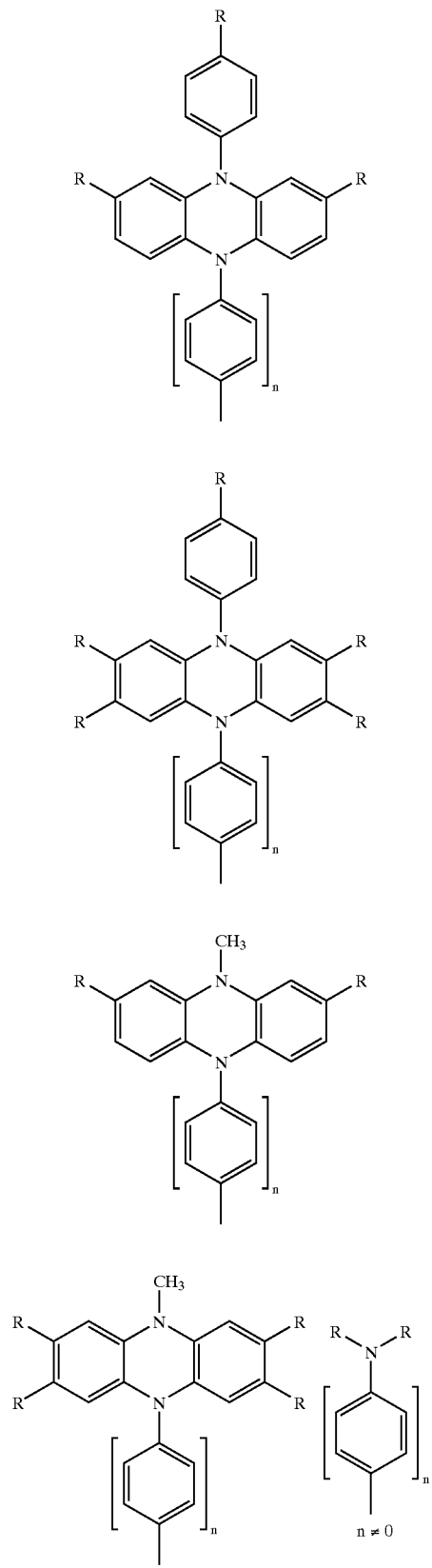
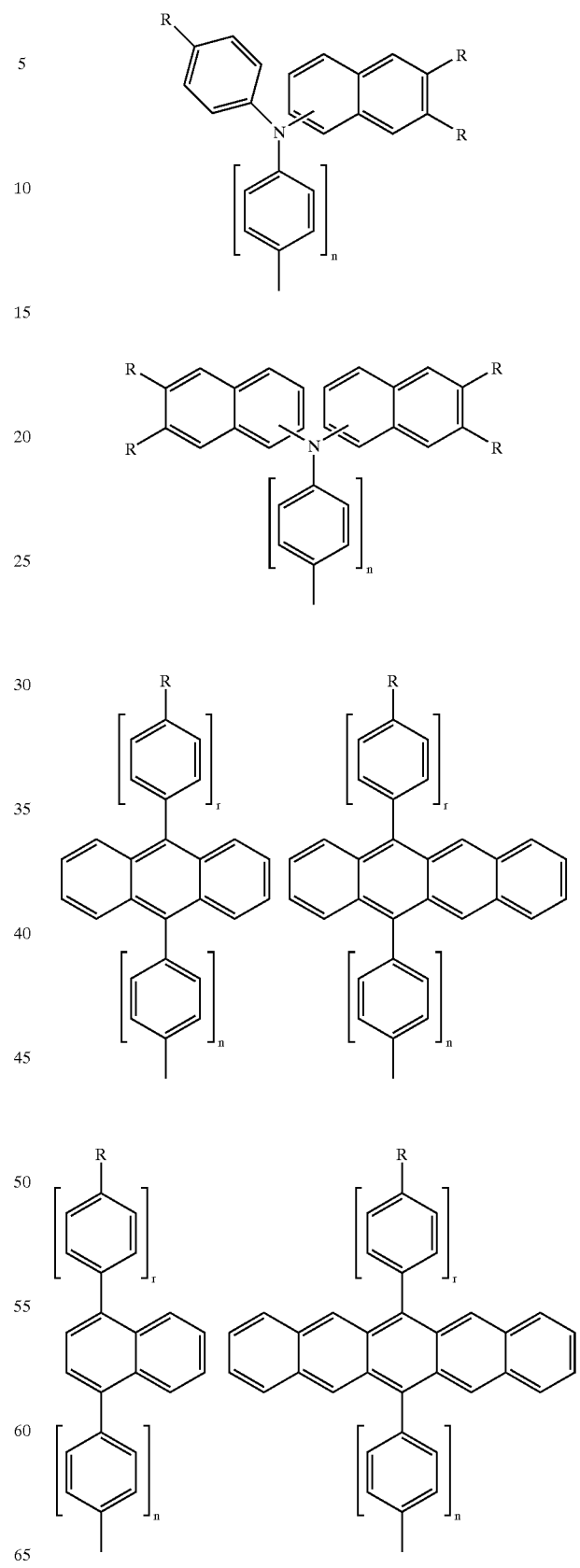
where the symbols and indices are as defined above,

II.b) $K^1 = N^1$ and is selected from the group consisting of:
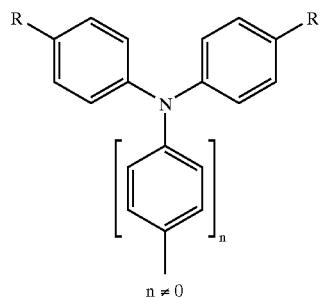
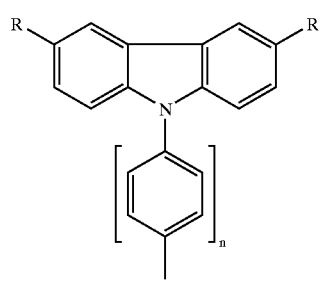
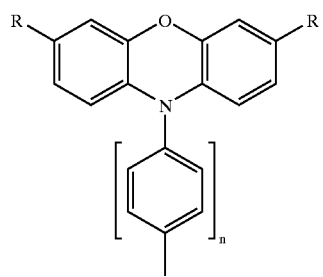
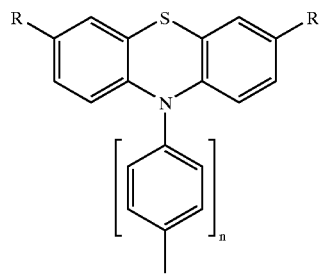
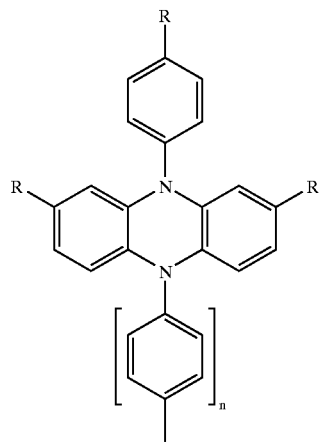
-continued
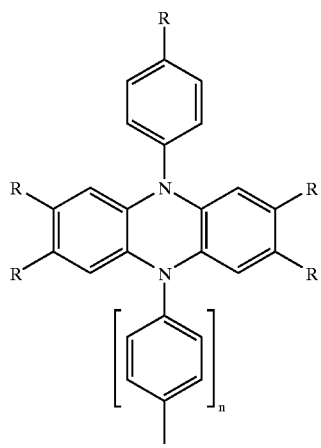
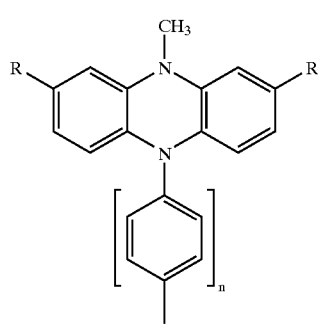
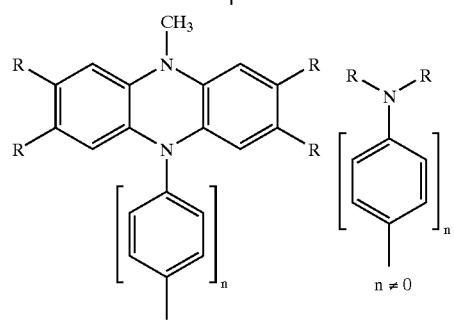
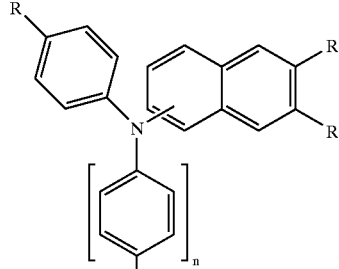
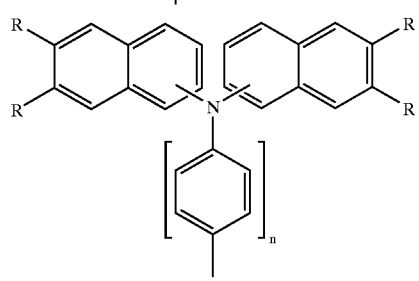

-continued
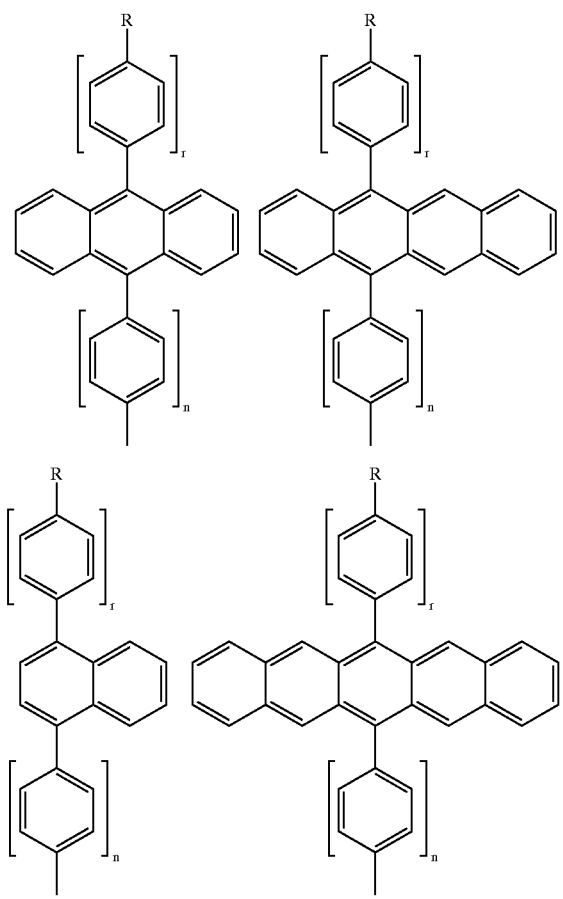
and L=M and is selected from the group consisting of:
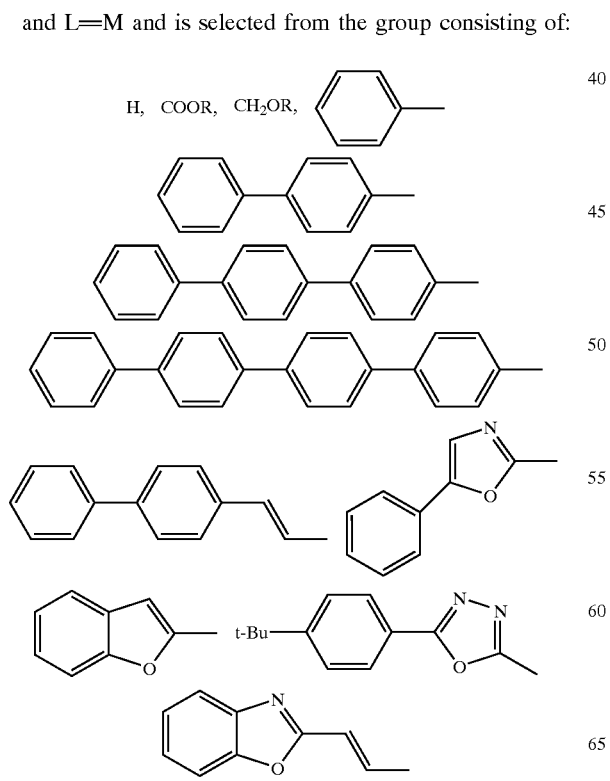
-continued
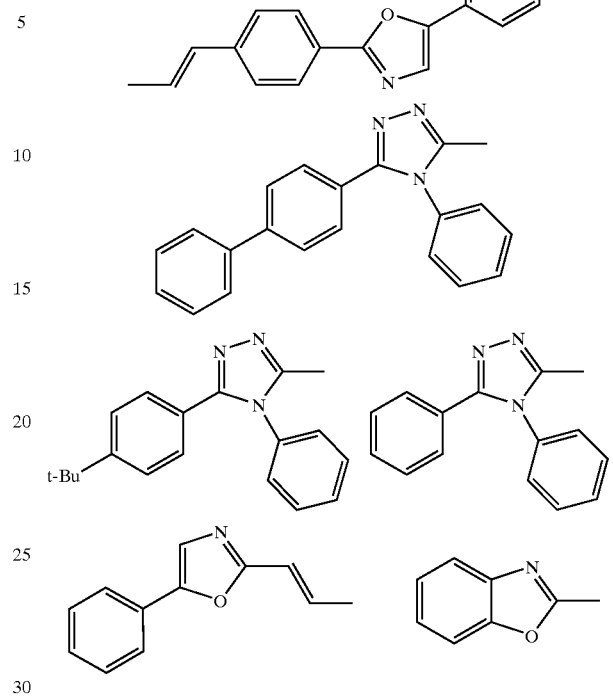
and Q, P$^1$ are identical or different and are selected from the group consisting of:
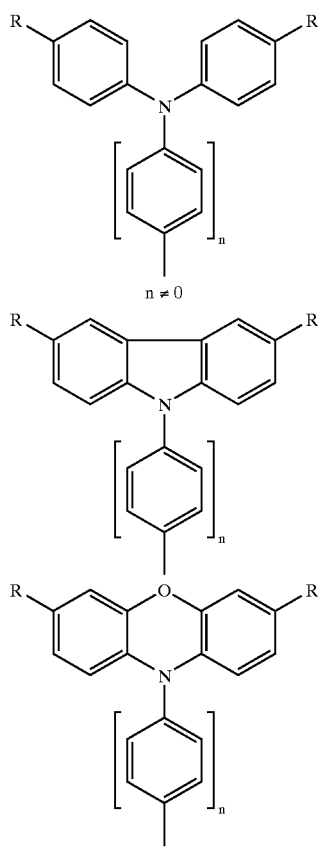

-continued
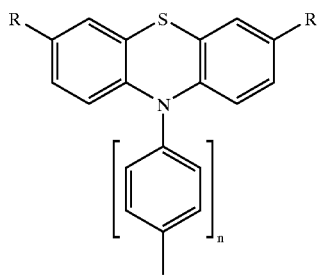
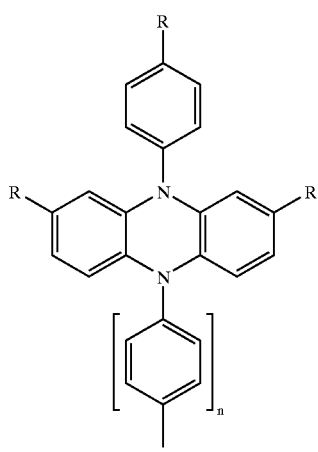
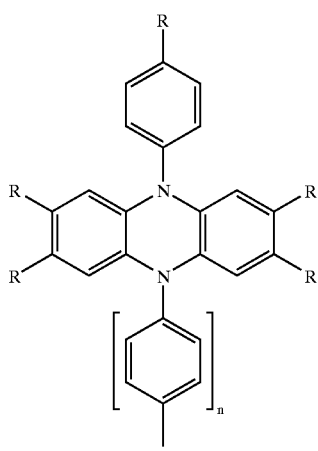
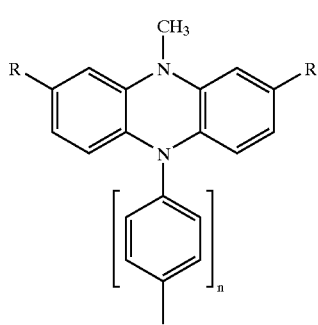
-continued
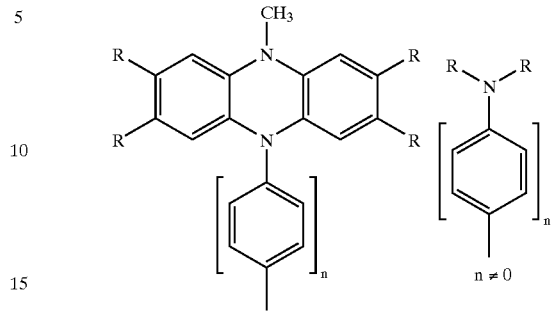
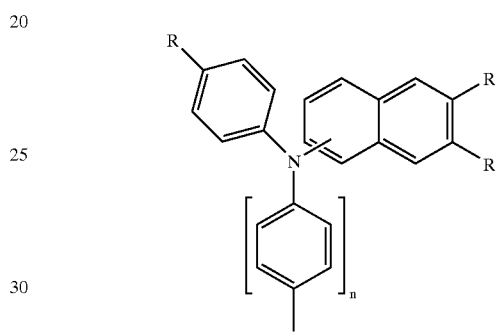
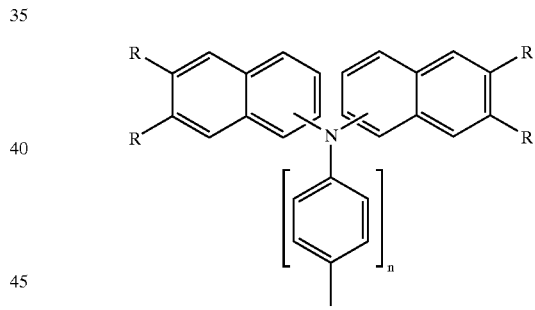
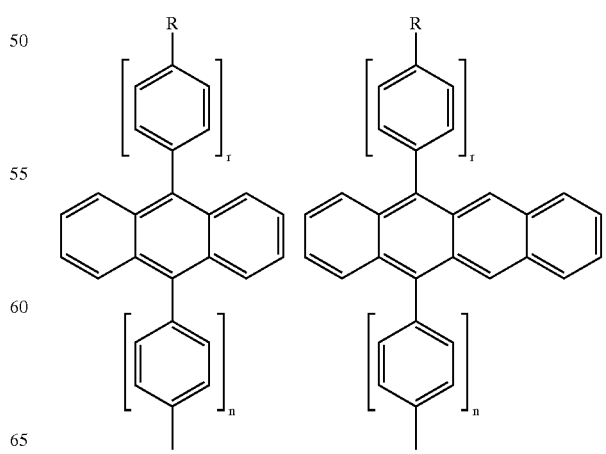

-continued
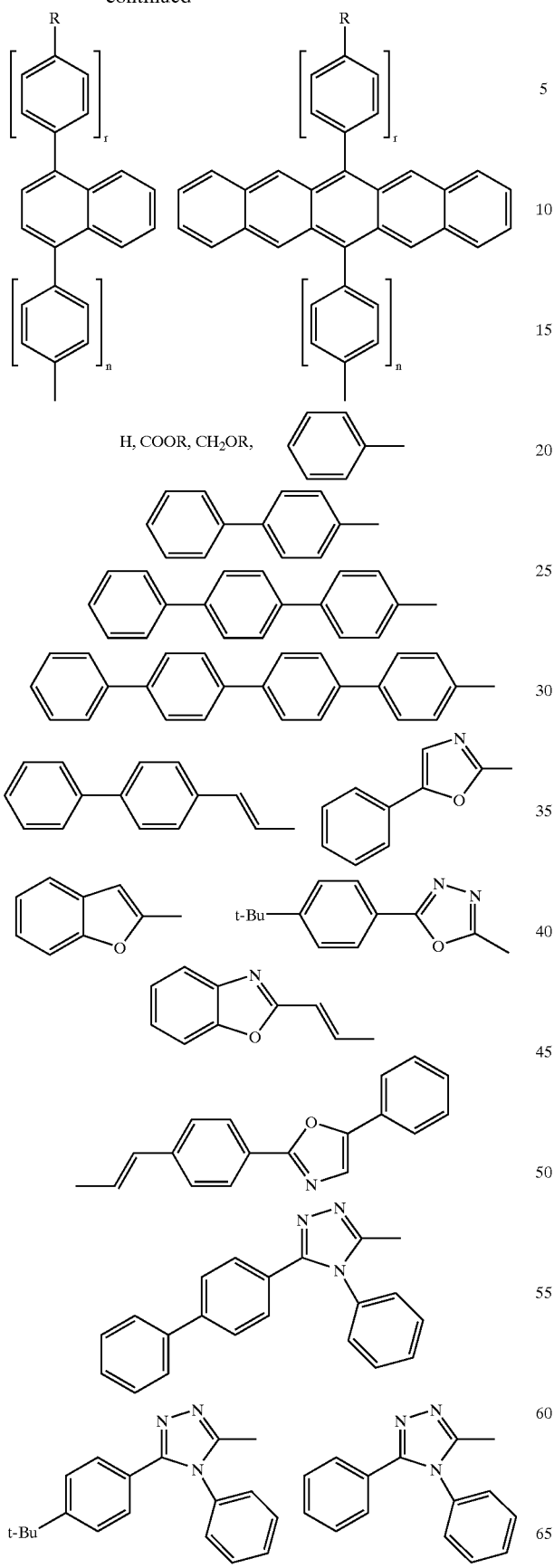
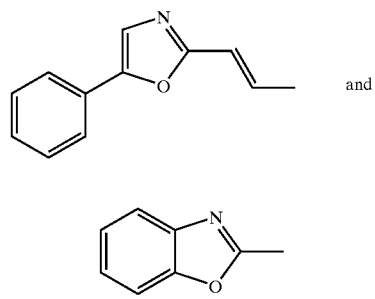
and
where the symbols and indices are as defined above;
11c) $K^1$=M and is selected from the group consisting of:
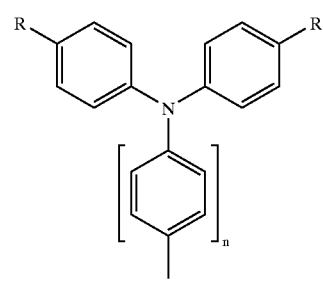
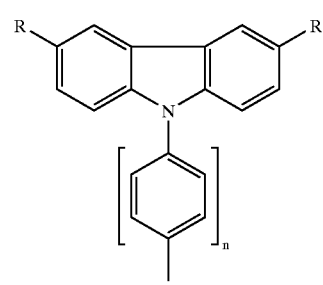
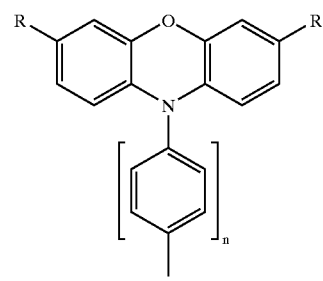
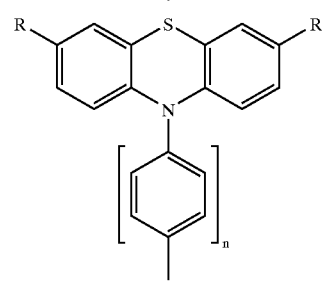

-continued
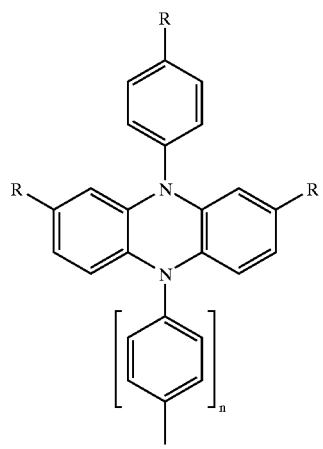
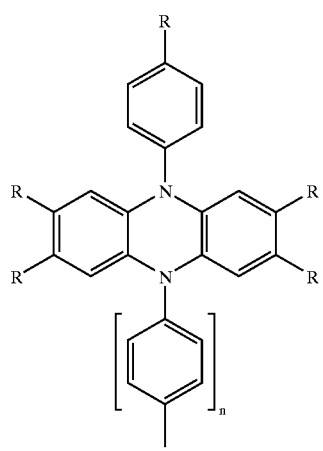
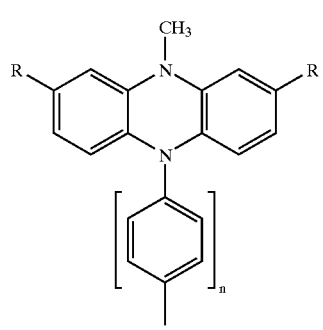
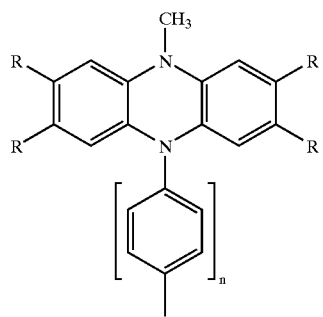
-continued
n≠0
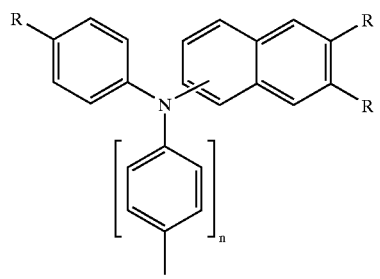
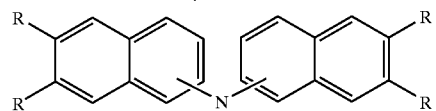
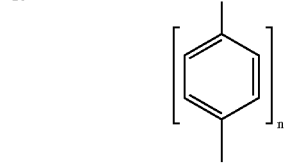
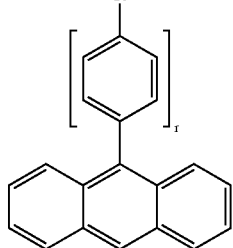
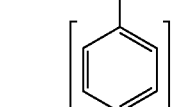
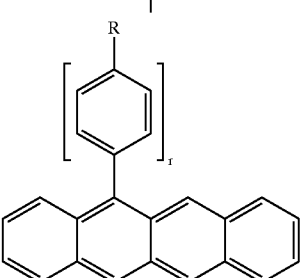
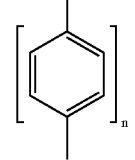

-continued
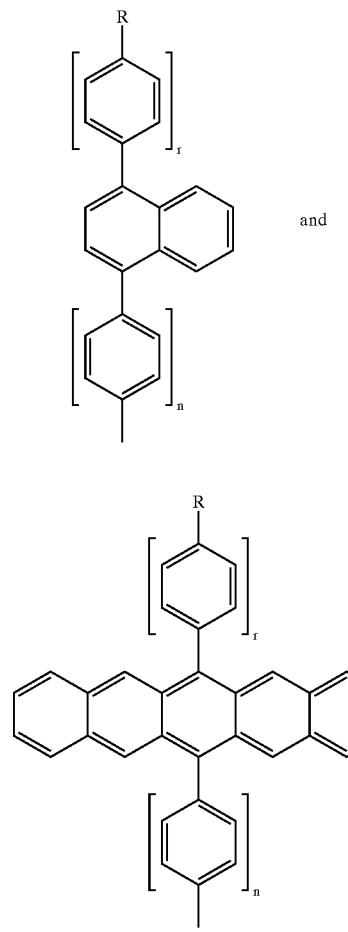
and
and M=N[1] and is selected from the group consisting of:
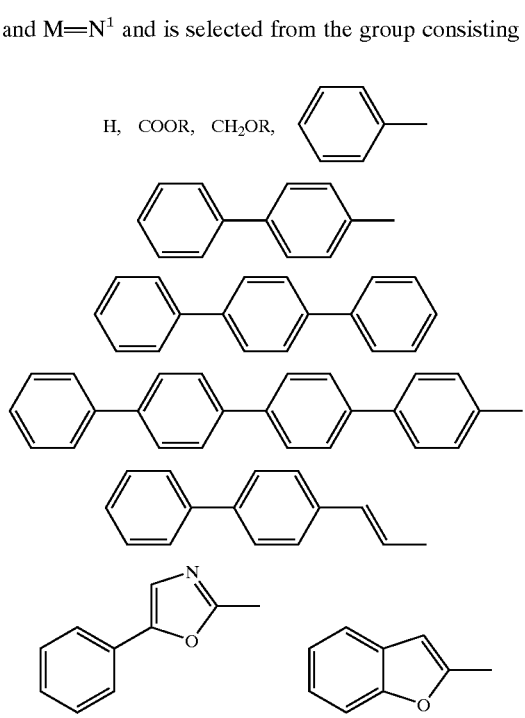
-continued
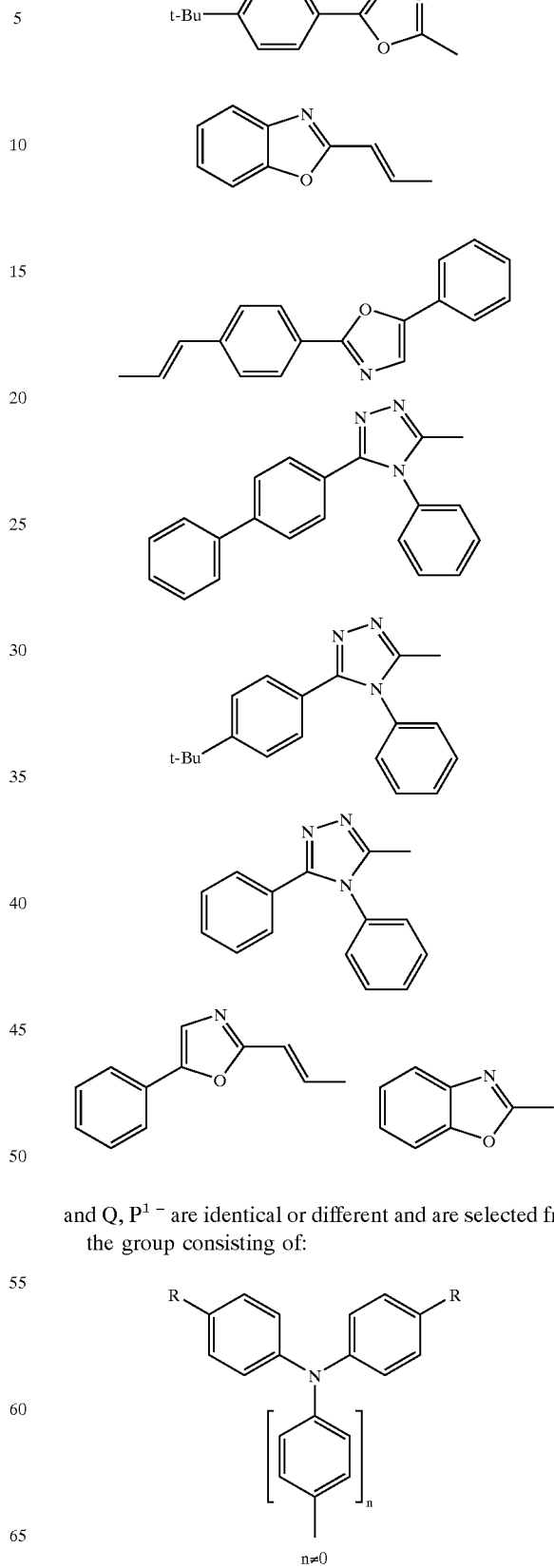
and Q, P[1]− are identical or different and are selected from the group consisting of:

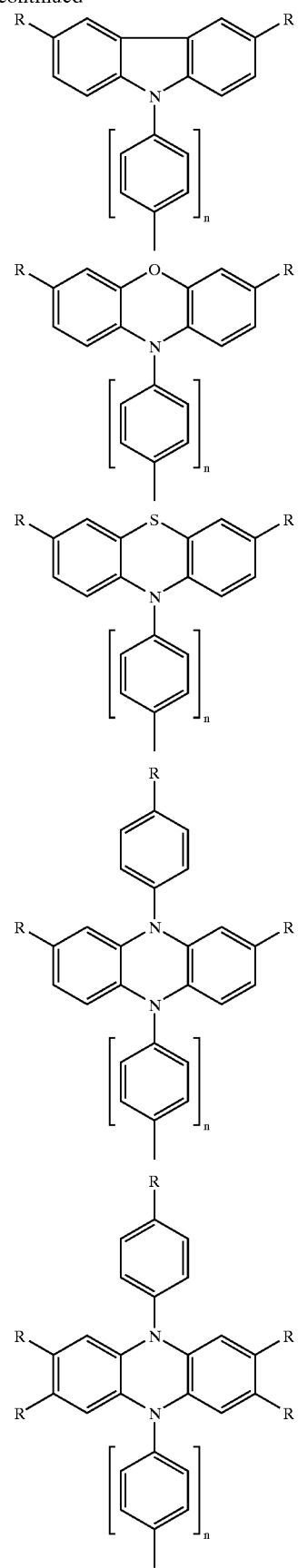
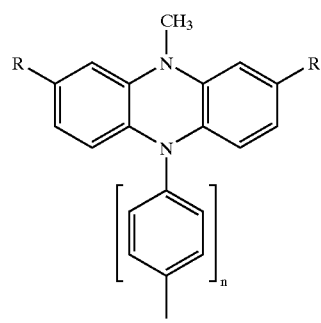
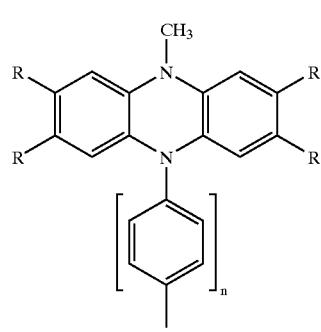
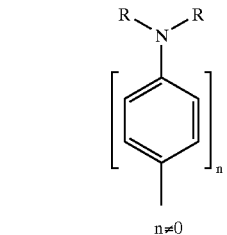
n≠0
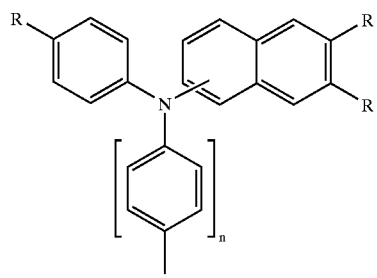
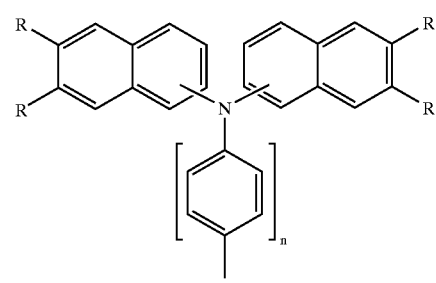

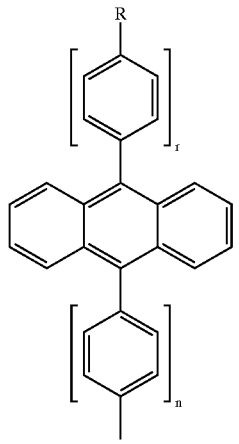
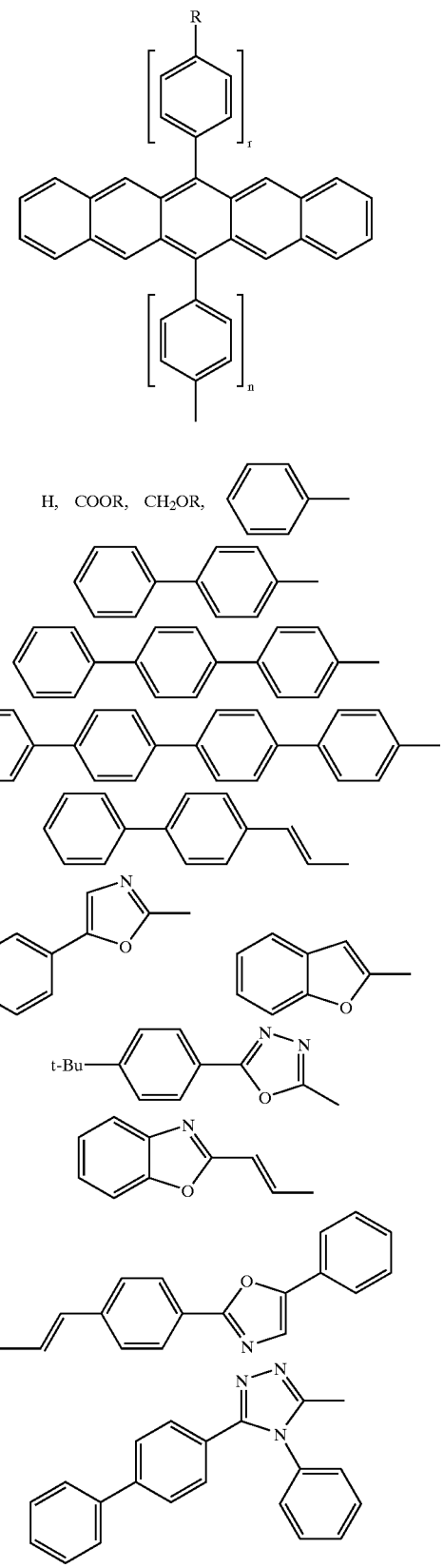

-continued
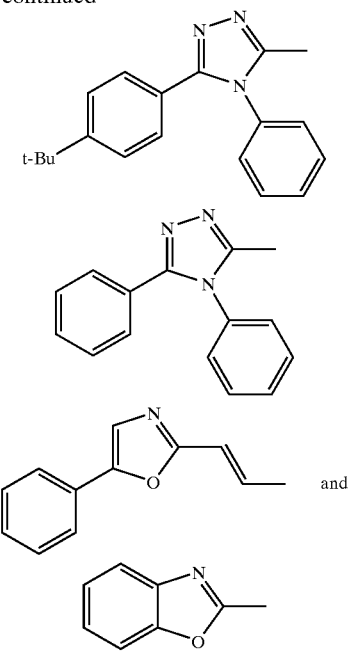
and
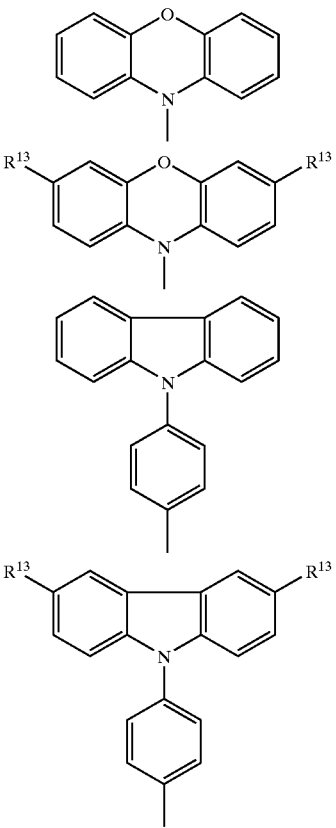
where the symbols and indices are as defined above.
3. A Spiro compound as claims in claim 1 selected from the group consisting of (II) aa, (II)ba and (II)ca.
II aa) $K^1$=L=M=$N^1$ and is selected from the group consisting of:
-continued
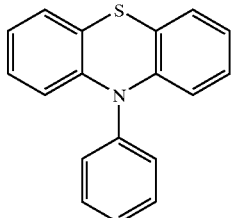
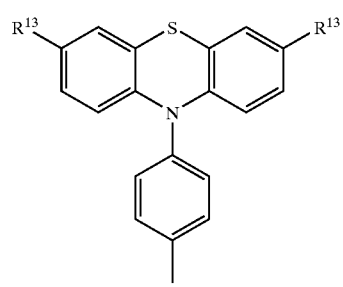
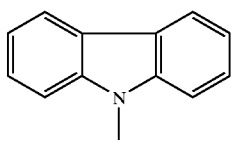
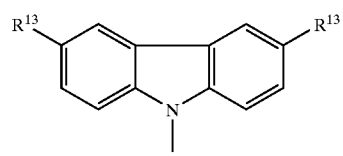
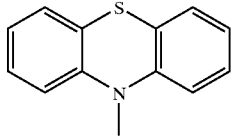
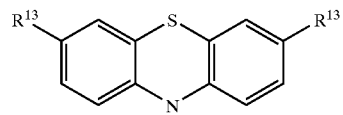
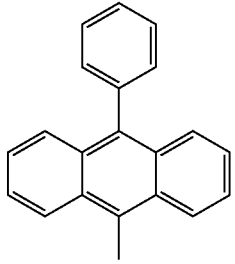

-continued
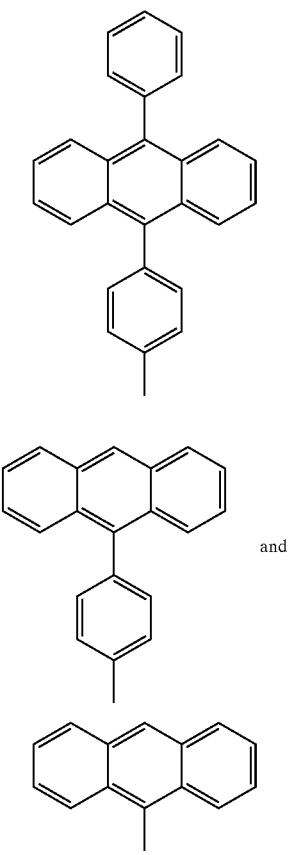
and
where $R^{13}$ is —O—CH$_3$, —O—C$_2$H$_5$, —S—CH$_3$, —S—C$_2$H$_5$;
and Q=P$^1$ and is selected from the goup consisting of:
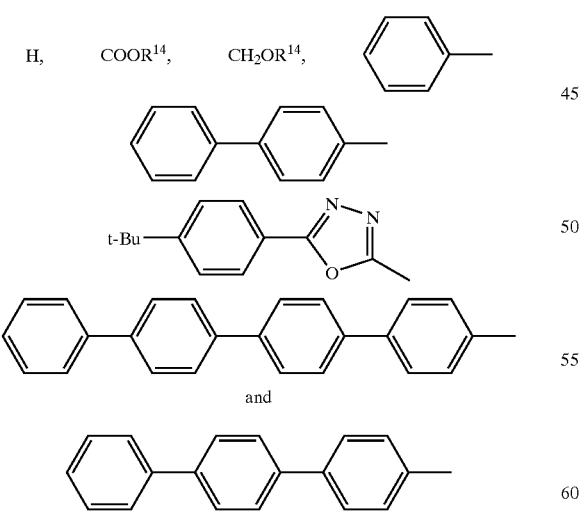
where $R^{14}$ is a straight-chain or branched alkyl group having from 1 to 12 carbon atoms;
II.ba) K$^1$=L=M=N$^1$=Q=P$^1$ and is selected from the group consisting of:
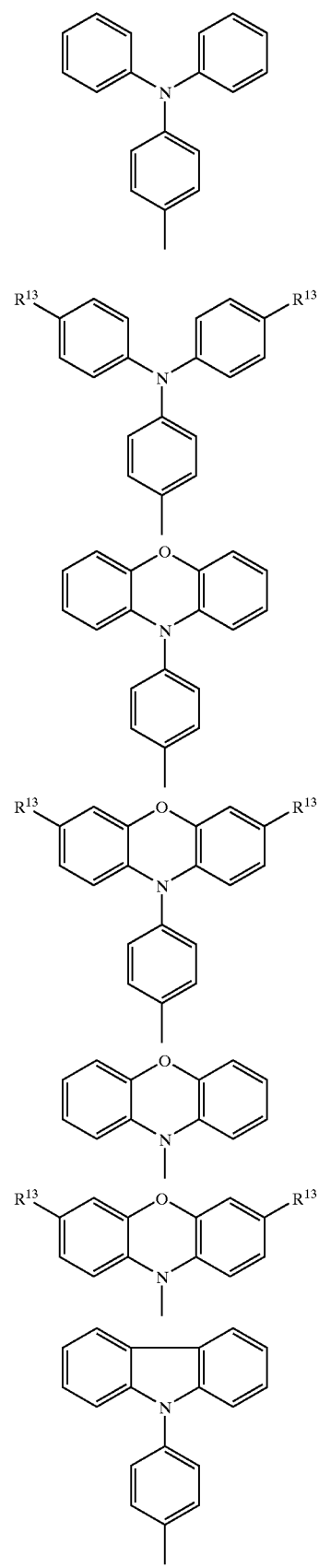

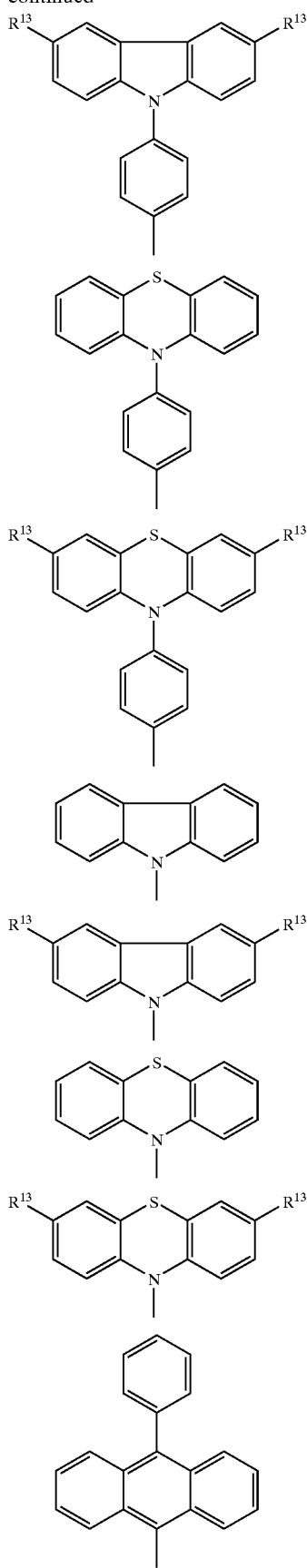
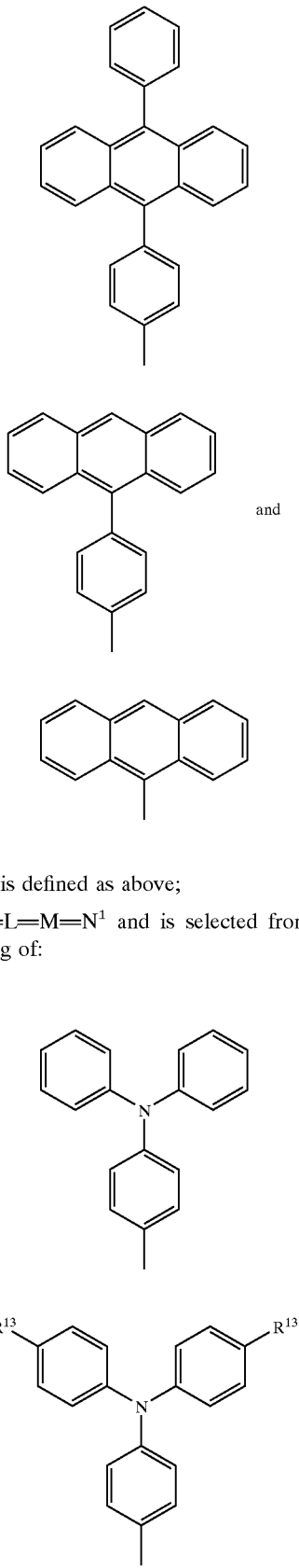
where $R^{13}$ is defined as above;
II.ca) $K^1=L=M=N^1$ and is selected from the group consisting of:

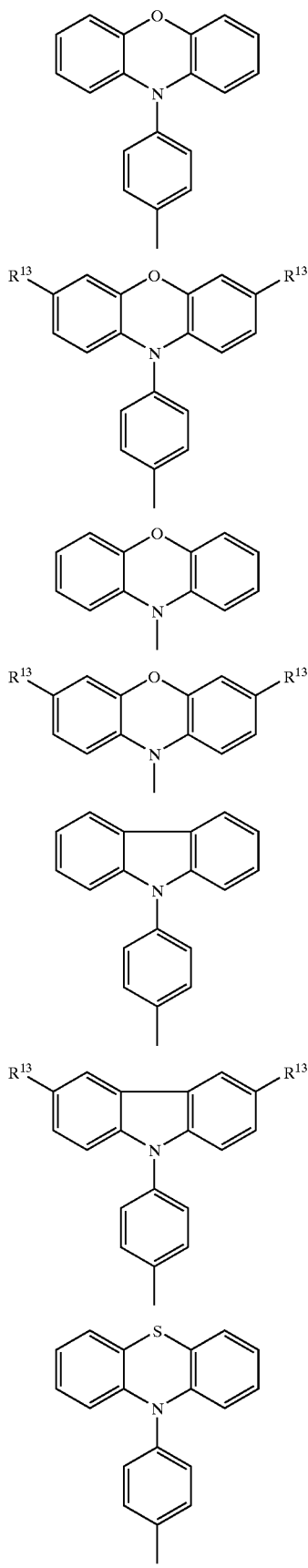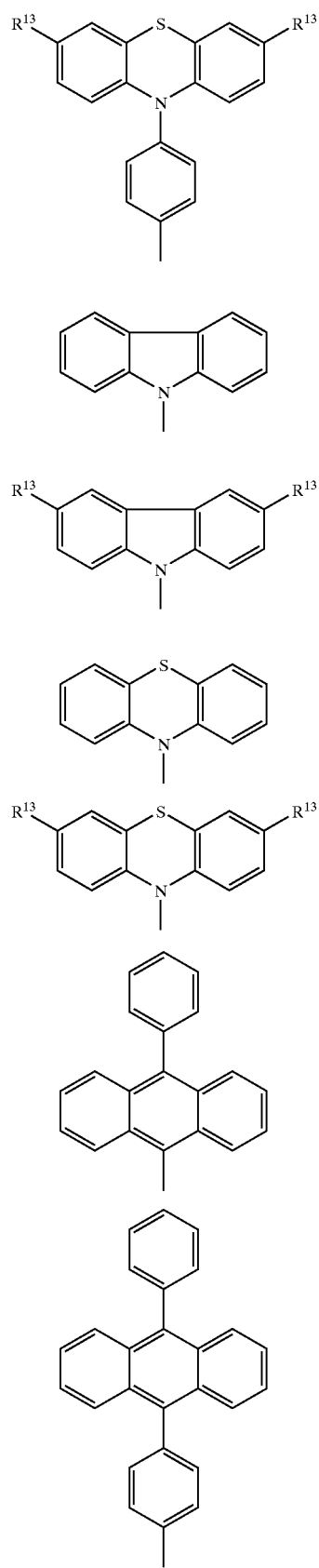

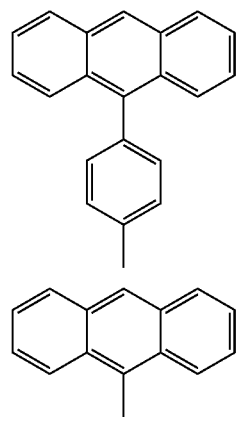

and Q=H and $P^1$ is selected from the group consisting of:

H, $COOR^{14}$, $CH_2OR^{14}$,

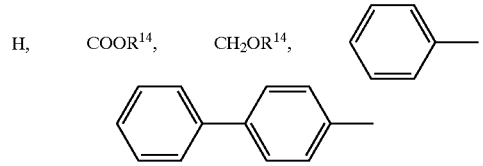

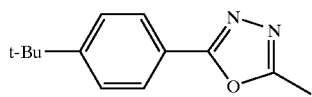

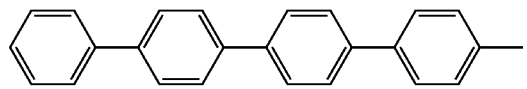

and

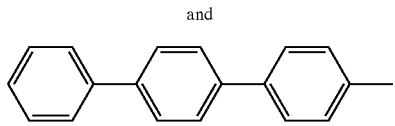

where $R^{13}$, $R^{14}$ are as defined above.

4. A charge transport material for a photovoltaic cell which comprises at least one amorphous spiro compound according to claim 1.

5. A photovoltaic cell which comprises a charge transport layer comprising the charge transport material according to claim 4.

* * * * *